United States Patent
Yoon et al.

(10) Patent No.: US 12,036,195 B2
(45) Date of Patent: Jul. 16, 2024

(54) CO-CRYSTALS OF NURR1-LBD IN COMPLEX WITH A CYCLOPENTENONE PROSTAGLANDIN AND MODULATORS OF NURR1

(71) Applicant: Nanyang Technological University, Singapore (SG)

(72) Inventors: Ho Sup Yoon, Singapore (SG); Sreekanth Rajan, Singapore (SG); Hui Ting Toh, Singapore (SG); Xuewei Liu, Singapore (SG); Hui Yao, Singapore (SG)

(73) Assignee: NANYANG TECHNOLOGICAL UNIVERSITY, Singapore (SG)

(*) Notice: Subject to any disclaimer, the term of this patent is extended or adjusted under 35 U.S.C. 154(b) by 0 days.

(21) Appl. No.: 17/850,014

(22) Filed: Jun. 27, 2022

(65) Prior Publication Data

US 2022/0331271 A1 Oct. 20, 2022

Related U.S. Application Data

(62) Division of application No. 16/334,550, filed as application No. PCT/SG2017/050476 on Sep. 20, 2017, now Pat. No. 11,406,610.

(30) Foreign Application Priority Data

Sep. 20, 2016 (SG) .......................... 10201607854Q

(51) Int. Cl.
| | | |
|---|---|---|
| A61K 31/191 | (2006.01) | |
| C07C 59/90 | (2006.01) | |
| C07K 14/705 | (2006.01) | |
| G16B 35/20 | (2019.01) | |

(52) U.S. Cl.
CPC ............ *A61K 31/191* (2013.01); *C07C 59/90* (2013.01); *C07K 14/70567* (2013.01); *G16B 35/20* (2019.02)

(58) Field of Classification Search
CPC . A61K 31/191; C07C 59/90; C07K 14/70567
See application file for complete search history.

(56) References Cited

U.S. PATENT DOCUMENTS

| | | | | |
|---|---|---|---|---|
| 2003/0119026 A1* | 6/2003 | Le | ........................ | C12Q 1/6883 435/325 |
| 2004/0214231 A1* | 10/2004 | Hashida | ............. | A61K 31/5575 435/7.1 |
| 2015/0111969 A1 | 4/2015 | Van Dross et al. | | |

FOREIGN PATENT DOCUMENTS

| | | | |
|---|---|---|---|
| CN | 1522699 | * | 8/2004 |
| CN | 1522699 A | | 8/2004 |
| JP | S61-151167 | | 7/1986 |
| WO | WO 03/047524 A2 | | 6/2003 |
| WO | WO 2016/044902 A1 | | 3/2016 |

OTHER PUBLICATIONS

Decressac et. al. (Nature Reviews Neurology (2013) 9:629-636). (Year: 2013).*
Kikuchi et. al. (Cancer and Metastasis Reviews (1994) 13:309-315). (Year: 1994).*
Wu et. al. (Endocrinology (2005) 146:237-246). (Year: 2005).*
Abeliovich, A. et al., *Midbrain Dopamine Neuron Differentiation: Factors and Fates*, Dev Biol 304, (2007) 447-454.
Ang, S. L., *Transcriptional Control of Midbrain Dopaminergic Neuron Development*, Development 133 (2006) 3499-3506.
Bartlett, P.A. et al., In Roberts, S.M., et al., (Eds.), *Chemical and Biological Problems in Molecular Recognition*, Royal Society of Chemistry, Cambridge (1989) 182-196.
Battye, T. G. G. B. et al., *iMOSFLM: A New Graphical Interface for Diffraction-Image Processing with MOSFLM*, Acta Crystallogr D Biol Crystallogr 67 (2011) 271-281.
Block, M. L. et al., *Microglia-Mediated Neurotoxicity: Uncovering the Molecular Mechanisms*, Nat Rev Neurosci 8 (2007) 57-69.
Bohm, H-J., *On the Use of LUDI to Search the Fine Chemicals Director for Ligands of Proteins of Known Three-Dimensional Structure*, J. Comp. Aided Molec. Design 8 (1994) 623-632.
Buervenich, S et al., *NURR1 Mutations in Cases of Schizophrenia and Manic-Depressive Disorder*, Am J Med Genet. 96 (2000) 808-813.
Carlsson, A. et al., *3,4-Dihydroxyphenylalanine and 5-Hydroxytryphophan as Reserpine Antagonists*, Nature 180 (Nov. 30, 1957) 1200.
Castillo, S. O. et al., *Dopamine Biosynthesis Is Selectively Abolished in Substantia Nigra/Ventral Tegmental Area But Not in Hypothalamic Neurons in Mice With Targeted Disruption of the Nurr1 Gene*, Mol Cell Neurosci 11 (1998) 36-46.
Chen, H. et al., *Nonsteroidal Antiinflammatory Drug Use and The Risk for Parkinson's Disease*, Ann Neurol 58 (2005) 963-967.
Chen, H. et al., *Nonsteroidal Anti-Inflammatory Drugs and the Risk of Parkinson Disease*, Arch Neurol 60 (2003) 1059-1064.
Chintharlapalli, S. et al., *Activation of Nur77 By Selected 1,1-Bis(3'-indolyl)-1-(p-substituted phenyl)Methanes Induces Apoptosis Through Nuclear Pathways*, J Biol Chem 280 (2005) 24903-24914 (2005).
Chu, Y. et al., *Age-Related Decreases in Nurr1 Immunoreactivity in the Human Substantia Nigra*, Journal of Comparative Neurology 450 (2002) 203-214.
Chu, Y. et al., *Nurr1 in Parkinson's Disease and Related Disorders*, The Journal of Comparative Neurology 494 (2006) 495-514.

(Continued)

*Primary Examiner* — Marcos L Sznaidman
(74) *Attorney, Agent, or Firm* — Alston & Bird LLP

(57) ABSTRACT

Co-crystals comprising the Nuclear receptor related 1 protein-ligand binding domain (Nurr1-LBD) and a cyclopentenone prostaglandin are provided. Also provided are methods of identifying or designing Nurr1-modulating ligands and compounds based on the crystal structures described herein as well as the applications of said ligands and compounds as Nurr1 modulators or medicaments.

3 Claims, 5 Drawing Sheets

Specification includes a Sequence Listing.

(56) References Cited

OTHER PUBLICATIONS

Clark, D. E. et al., *Pro_Ligand: an approach to De Novo Molecular Design. 1. Application to the Design of Organic Molecules*, J. Comp. Aided Molec. Design 9 (1995) 13-32.
Codina, A. et al., *Identification of a Novel Co-regulator Interaction Surface on the Ligand Binding Domain of Nurr1 Using NMR Footprinting*. The Journal of Biological Chemistry, vol. 279, No. 51 (Sep. 28, 2004) 53338-53345.
Collins, L. et al., *Parkinson's Disease: Diagnosis and Current Management*, Prescriber 26 (2015) 16-23.
Colman, P. M., *Structure-Based Drug Design*, Current Opinion in Struc. Biol. 4 (1994) 868-874.
Dauer, W. et al., *Parkinson's Disease: Mechanisms and Models*, Neuron 39 (Sep. 11, 2003) 889-909.
De Vera, I. M. et al., *Identification of a Binding Site for Unsaturated Fatty Acids In the Orphan Nuclear Receptor Nurr1*, ACS Chemical Biology (2016).
Emsley, P. et al., *Coot: Model-Building Tools for Molecular Graphics*, Acta Crystallogr D Biol Crystallogr 60 (2004) 2126-2132 (2004).
Evans, P., *Scaling and Assessment of Data Quality*, Evans, Acta Crystallogr D Biol Crystallogr 62 (2006) 72-82.
Farrer, M. J., *Genetics of Parkinson Disease: Paradigm Shifts and Future Prospects*, Nature Reviews Genetics, vol. 7 (Apr. 2006) 306-318.
Forman, B. M. et al., *Nuclear Hormone Receptors Activate Direct, Inverted, and Everted Repeats*, Annals of the New York Academy of Sciences 761 (1995) 29-37.
Gai, W. P. et al., *In Situ and In Vitro Study of Colocalization and Segregation of α-Synuclein, Ubiquitin, and Liquids in Lewy Bodies*, Exp Neurol 166 (2000) 324-333.
Germain, P. et al., *Overview of Nomenclature of Nuclear Receptors*, Pharmacological Reviews 58 (2006) 685-704.
Glass, C. K. et al., *Mechanisms Underlying Inflammation in Neurodegeneration*, Cell 140 (2010) 918-934.
Goodford, P. J., *A Computational Procedure for Determining Energetically Favorable Binding Sites on Biologically Important Macromolecules*, J. Med. Chem. 28 (1985) 849-857.
Goodsell, D. S. et al., *Automated Docking of Substrates to Proteins by Simulated* Annealing, Proteins: Structure, Function, and Genetics 8 (1990) 195-202.
Greenamyre, J. T. et al., *The Rotenone Model of Parkinson's Disease: Genes, Environment and Mitochondria*, Parkinsonism Relat Disord 9, (2003) S59-S64.
Grimes, D. A. et al., *Translated Mutation in the Nurr1 Gene as a Cause for Parkinson's Disease* Mov Disord 21 (2006) 906-909.
Guida, W. C., *Software for Structure-Based Drug Design*, Current Opinion in Struc. Biol. 4 (1994) 777-781.
Guo, J. et al. *Clinicopathological Significance of Orphan Nuclear Receptor Nurr1 Expression in Gastric Cancer*, Clin Transl Oncol 17 (2015) 788-794.
Heikkila, R. E., et al., *Dopaminergic Toxicity of Rotenone and The 1-methyl-4-phenylpyridinium Ion After Their Stereotaxic Administration to Rats: Implication for the Mechanism of 1-methyl-4-phenyl-1,2,3,6-tetrahydropyridine Toxicity*, Neurosci Lett 62 (1985) 389-394.
Hering, R. et al., *Extended Mutation Analysis and Association Studies of Nurr1 (NR4Aw) In Parkinson Disease*, Neurology 62 (2004) 1231-1232.
Hintermann, S. et al., *Identification of a Series of Highly Potent Activators of the Nurr1 Signaling Pathway*, Bioorganic & medicinal Chemistry Letters 17 (2007) 193-196.
Hirsch, E. C. et al., *Neuroinflammation in Parkinson's Disease: A Target for Neuroprotection?*, Lancet Neurol 8 (2009) 382-397.
Hitomi, M. et al., *Prostaglandin A2 Blocks The Activation of GI Phase Cyclin-Dependent Kinase Without Alterin Mitogen-Activated Protein Kinase Stimulation*, J Biol Chem 271 (1996) 9376-9383.

Holla, V. R. et al., *Prostaglandin E2 Regulates the Nuclear Receptor NR4A2 in Colorectal Cancer*, J Biol Chem., vol. 281, No. 5 (Feb. 3, 2006) 2676-2682.
Hughes, T. S. et al., *An Alternate Binding Site for PPARgamma Ligands*, Nature Communications 5 (2014) 3571.
Inamoto, T. et al., *Cytoplasmic Mislocalization of the Orphan Nuclear Receptor Nurr1 Is a Prognostic Factor in Bladder Cancer*, Cancer 116 (Jan. 15, 2010) 340-346.
Itoh, T. et al., *Structural basis for the activation of the PPARgamma by Oxidized Fatty Acids*, Nature Structural & Molecular Biology 15 (2008) 924-931.
Kadkhodaei, B. et al., *Nurr1 is Required for Maintenance of Maturing and Adult Midbrain Dopamine Neurons*, J Neurosci 29 (2009) 15923-15932.
Kagaya, S. et al., *Prostaglandin A2 Acts as a Transactivator for NOR1 (NR4A3) Within the Nuclear Receptor Superfamily*, Biological and Pharmaceutical Bulletin, vol. 28, No. 9 (Jun. 15, 2005) 1603-1607.
Kim, C-H. et al., Nuclear Receptor Nurr1 Aagonists Enhance Its Dual Functions and Improve Behavioral Deficits in an Animal Model of Parkinson's Disease. Proceedings of the National Academy of Sciences of the United States of America, Jun. 29, 2015, vol. 112, No. 28, pp. 8756-8761.
Kuntz, I. D. et al., *Structure-Based Molecular Design*, Accounts of Chemical Research, vol. 27, No. 5 (May 1994) 117-123.
Lang, A. E. et al., *Parkinson's Disease*, The New England Journal of Medicine, vol. 339, No. 15, Part 1, (Oct. 8, 1998) 1044-1053.
Lang, A. E. et al., *Parkinson's Disease*, The New England Journal of Medicine, vol. 339, No. 16, Part 2, (Oct. 15, 1998) 1130-1143.
Langston, J. W. et al., *Chronic Parkinsonism in Humans Due to a Product of Meperidine-Analog Synthesis*, Science 219 (1983) 979-980.
Law, S. W. et al., *Identification of a New Brain Specific Transcription Factor, NURR1*, Molecular Endocrinology 6 (1992) 2129-2135.
Le, W.-D. et al., *Mutations in NR4A2 Associated with Familial Parkinson Disease*, Nature Genetics 33 (2003) 85-89.
Lebedev, A. A. et al., *JLigand: A Grpahical Tool for the CCP4 Template-Restraint Library*, Acta Crystallogr D Biol Crystallogr 68 (2012) 431-440.
Lesser, R. P. et al., *Analysis of the Clinical Problems in Parkinsonsism and the Complications of Long-Term Levodopa Therapy*, Neurology 29 (Sep. 1979) 1253-1260.
Lee, S. Y. et al., *prostaglandin A2 Activates Intrinsic Apoptotic Pathway by Direct Interaction With Mitochondria in HL-60 Cells*, Prostaglandins & other Lipid Mediators 91 (2010) 30-37.
Lima, I. v. et al.,*Role of Prostaglandins in Neuroinflammatory and Neurodegenerative Diseases*, Mediators of Inflammation 2012 (2012) 946813.
Liu, Z. et al. *A Drosophila Model for LRRK2-Linked Parkinsonism*, Proc Natl Acad Sci U S A 105 (2008) 2693-2698.
Llopis, S. et al., *Dichotomous Roles for the Orphan Nuclear Receptor NURR1 in Breast Cancer*, BMC Cancer 13:139 (2013) 9 pages.
Maira, M. et al., *Heterodimerization Between Members of the Nur Subfamily of Orphan Nuclear Receptors as a Novel Mechanism for Gene Activation*, Molecular and Cellular Biology, vol. 19, No. 11 (Nov. 1999) 7549-7557.
Marini, S. et al., *Growth Inhibition of Friend Erythroleukaemia Cell Tumours In Vivo by a Synthetic Analogue of Prostaglandin A: An Action Independent of Natural Killer Activity*, British Journal of Cancer 61 (1990) 394-399.
McCoy, A. J. et al., *Phaser Crystallographic Software*, J Appl Crystallogr 40 (2007) 658-674.
McEvoy, A. N. et al., *Activation of Nuclear Orphan Receptor NURR1 Transcription by Nf-κB and Cyclic Element-Binding Protein in Rheumatoid Arthritis Synovial Tissue*, J Immun. 168 (2002) 2979-2987.
Mcgeer, P. L. et al., *Glial Reactions in Parkinson's Disease*, Mov Disord 23 (2008) 474-483.
Mcgeer, P. L. et al., *Reactive Microglia are Positive for HLA-DR in the Substantia Nigra of Parkinson's and Alzheimer's Disease Brains*, Neurology 38 (1988) 1285-1291.

(56) References Cited

OTHER PUBLICATIONS

Meng, E. C. et al., *Automated Docking With Grid-Based Energy Evaluation*, J. Compt. Chem. 13 (1992) 505-524.
Miller, M. D. et al., *FLOG: A System to Select 'Quasi-Flexible' Ligands Complementary to a Receptor of Known Three-Dimensional Structure*, J. Comp. Aided Molec. Design 8 (1994) 153-174.
Miranker, A. et al., *Functionality Maps of Binding Sites: A Multiple Copy Simultaneous Search Method*, Proteins: Structure, Function, and Genetics 11 (1991) 29-34.
Mohan, H. M. et al.,*Molecular Pathways: The Role of NR4A Orphan Nuclear Receptors in Cancer*, Clin Cancer Res 18 (2012) 3223-3228.
Moon et al., *Correlation Between Orphan Nuclear Receptor Nurr1 Expression and Amyloid Deposition in 5XFAD Mice, An Animal Model of Alzheimer's Disease*, J Neurochem 132 (2015) 254-262.
Muller, T. et al., *Inhibition of Catechol-O-Methyltransferase contributes to More Stable Levodopa Plasma Levels*, Mov Disord 21 (2006) 332-336.
Murshudov, G. N. et al., *REFMAC5 for the Refinement of Macromolecular Crystal Structures*, Acta Crystallogr D Biol Crystallogr 67 (2011) 355-367.
Musiek, E. S. et al., *Cyclopentenone Eicosanoids as Mediators of Neurodegeneration: A Pathogenic Mechanism of Oxidative Stress-mediated and Cyclooxygenase-Mediated Neurotoxicity*, Brain Pathology 15 (2005) 149-158.
Nagatsu, T. et al., *Inflammatory Process in Parkinson's Disease: Role for Cytokines*, Curr Pharm Des 11, (2005) 999-1016.
Ng, C. H. et al., *Parkin Protects Against LRRK2 G2019S Mutant-Induced Dopaminergic Neurodegeneration In Drosophila*, J Neurosci 29 (2009) 11257-11262.
Nichols, W. C. et al., *Evaluation of the Role of Nurr1 in a Large Sample of Familial Parkinson's Disease*, Mov Disord 19 (2004) 649-655.
Ordentlich, P. et al., *Identification of the Antineoplastic Agent 6-Mercaptopurine as An Active of the orphan Nuclear Hormone Receptor Nurll*, Journal of Biological Chemistry 278 (2003) 24791-24799.
Paulsen, R. F. et al., *Three Related Brain Nuclear Receptors, NGFI-B, Nurr1, and NOR-1, As Transcriptional Activators*, Journal of Molecular Neuroscience: MN 6 (1995) 249-255.
Pearen, M. A. et al., *Minireview: Nuclear Hormone Receptor 4A Signaling: Implications for Metabolic Disease*, Molecular Endocrinology (Baltimore, Md.) 24 (2010) 1891-1903.
Perlmann, T. et al., *A Novel Pathway for Vitamin A Signaling Mediated by RXR Heterodimerization With NGFI-B and NURR1*, Genes & Development 9 (1995) 769-782.
Pettersen, E. F. et al., *UCSF Chimera—A Visualization System for Exploratory Research and Analysis*, J Comput Chem. 25 (2004) 1605-1612.
Powers, K. M. et al., *Combined Effects of Smoking, Coffee, and NSAIDs on Parkinson's Disease Risk*, Mov Disord 23 (2008) 88-95.
Reynolds, A. D. et al., *Nitrated Alpha-Synuclein-Activated Microglial Profiling for Parkinson's Disease*, J Neurochem 104 (2008) 1504-1525.
Reynolds, A. D. et al., *Nitrated Alpha-Synuclein and Microglial Neuroregulatory Activities*, J Neuroimmune Pharmacol 3 (2008) 59-74.
Qin, Z. H. et al., *Prostaglandin A(1) Protects Striatal Neurons Against Excitotoxic Injury In Rat Striatum*, J Pharmacol Exp Ther 297 (2001) 78-87.
Ranhotra, H. S., *The NR4A Orphan Nuclear Receptors: Mediators In Metabolism and Diseases*, Recept Signal Transduct Res. 35 (2015) 184-188.
Rojas, P. et al., *Adult Mice With Reduced Nurr1 Expression: An Animal Model for Schizophrenia*, Mol Psychiatry. 12 (2007) 756-766.
Saucedo-Cardenas, O. et al., *Nurr1 Is Essential For the Induction of the Dopaminergic Phenotype and the Survival of Ventral Mesencephalic Late Dopaminergic Precursor Neurons*, Proc Natl Acad Sci U S A 95 (1998) 4013-4018.
Shashidharan, P. et al., *TorsinA Accumulation in Lewy Bodies in Sporadic Parkinson's Disease*, Brain research 877 (2000) 379-381.
Sherman, M. Y. et al., *Cellular Defenses Against Unfolded Proteins: A Cell Biologist Thinks About Neurodegenerative Diseases*, Neuron 29, (2001) 15-32.
Smidt, M. P. et al., *How to Make a Mesodiencephalic Dopaminergic Neuron*, Nat Rev Neurosci 8 (2007) 21-32.
Smith, A. G. et al., *Regulation of NR4A Nuclear Receptor Expression by Oncogenic BRAF In Melanoma Cells*, Pigment Cell & Melanoma Research, vol. 24, Issue 3 (2011) 551-563.
Smits, S. M. et al., *Involvement of Nurr1 in Specifying the Neurotransmitter Identity of Ventral Midbrain Dopaminergic Neurons*, Eur J Neurosci 18 (2003) 1731-1738.
Steiner, J. A. et al., *A Deadly Spread: Cellular Mechanisms of Alpha-Synuclein Transfer*, Cell Death Differ 18 (2011) 1425-1433.
Streit, W. J., *Microglia as Neuroprotective, Immunocompetent Cells of the CNS*, Glia 40 (2002) 133-139.
Sweet, R. D. et al., *Five Years' Treatment of Parkinson's Disease With Levodopa, Therapeutic Results and Survival of 100 Patients*, Ann Intern Med 83 (1975) 456-463.
Tansey, M. G., et al., *Neuroinflammatory Mechanisms in Parkinson's Disease: Potential Environmental Triggers, Pathways, and Targets for Early Therapeutic Intervention*, Exp Neurol 208 (2007) 1-25.
Wallen, A. et al., *Transcriptional Control of Dopamine Neuron Development*, Ann N Y Acad Sci 991 (2003) 48-60.
Wallen, A. A. et al., *Orphan Nuclear Receptor Nurr1 is Essential for Ret Expression in Midbrain Dopamine Neurons and in the Brain Stem*, Mol Cell Neurosci 18 (2001) 649-663.
Wang, J. et al., *Orphan Nuclear Receptor Nurr1 as a Potential Novel Marker for Progression in Human Prostate Cancer*, Asian Pac J Cancer Prev. 14 (2013) 2023-2028.
Wang, S. et al. *Prostaglandin A1 Inhibits Rotenone-Induced Apoptosis in SH-SY5Y Cells*, J. Neurochem 83 (2002) 1094-1102.
Winn, M. D. et al., *Overview of the CCP4 Suite and Current Developments*, Acta Crystallogr D Biol Crystallogr 67 (2011) 235-242 (2011).
Xing, G. et al., *Reduction of Dopamine-Related Transcription Factors Nurr1 and NGFI-B in the Prefrontal Cortex in Schizophrenia and Bipolar Disorders*, Schizophrenia Research 84 (2006) 36-56.
Zetterström, R. H. et al., *Dopamine Neuron Agenesis in Nurr1-Deficient Mice*, Science 276 (1997) 248-250.
Zetterstrom, R. H. et al., *Retinoid X Receptor Heterodimerization and Developmental Expression Distinguish the Orphan Nuclear Receptors NGFI-B, Nurr1, and Nor1*, Molecular Endocrinology (Baltimore, Md) 10 (1996) 1656-1666.
Zhan, Y. et al., *Cytosporone B Is An Agonist for Nuclear Orphan Receptor Nur77*, Nat Chem Biol 4 (2008 ) 548-556.
Zhang, H. L. et al., *Neuroprotective Effects of Prostaglandin A1 In Animal Models of Focal Ischemia*, Brain Res 1039 (2005) 203-206.
Zhang, W. et al., *Aggregated Alpha-Snuclein Activates Microglia: A Process Leading to Disease Progression in Parkinson's Disease*, Faseb J 19 (2005) 533-542.
Zheng, K. et al., *A Common NURR1 Polymorphism Associated With Parkinson Disease and Diffuse Lewy Body Disease*, Arch Neurol 60 (2003) 722-725.
International Search Report and Written Opinion for Application No. PCT/SG2017/050476 dated Dec. 11, 2017 (10 pages).
Morissette (Advanced Delivery Reviews (2004) 56:275-300). (Year: 2004).
Vippagunta (Advanced Drug Delivery Reviews (2001) 48:3-26). (Year 2001).
Kuntz I.D. et al., *A Geometric Approach to Macromolecule-Ligand Interactions*, J. Mol. Biol. 161 (1982) 269-288.
Wang, Z et al., *Structure and Function of Nurr1 Identifies a Class of Ligand-Independent Nuclear Receptors*, Nature 9 (2003) 555-560.

\* cited by examiner (a)

(b)

CO-CRYSTALS OF NURR1-LBD IN COMPLEX WITH A CYCLOPENTENONE PROSTAGLANDIN AND MODULATORS OF NURR1

CROSS-REFERENCE TO RELATED APPLICATIONS

This application is a divisional of U.S. application Ser. No. 16/334,550, which is the national phase application filed under 35 U.S.C. § 371 of International Application No. PCT/SG2017/050476, filed on Sep. 20, 2017, which application claims the benefit of priority of Singapore Patent Application No. 10201607854Q, filed on Sep. 20, 2016, the contents of which are incorporated herein by reference in their entirety for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to co-crystals comprising the Nuclear receptor related 1 protein-ligand binding domain (Nurr1-LBD) and a cyclopentenone prostaglandin and methods of identifying, designing, and using Nurr1-modulating ligands and compounds.

BACKGROUND OF THE INVENTION

Parkinson's disease (PD) is a neurodegenerative disorder caused by progressive and selective degeneration of midbrain dopamine (mDA) neurons, which affects approximately 0.3% of the general population and 1-2% of the population over age 65. There are no treatments that can halt or slow down the progression of the disease process. Currently available treatments are only symptomatic.

Over the years, extensive progress has been made in the understanding of how key signaling molecules and transcription factors orchestrate the development of mDA neurons in the brain.

Development of mDA neurons is dependent on Sonic hedgehog (Shh) and Wnt1 and their downstream factors. Notably, these two pathways (i.e., Shh-FoxA2 and Wnt1-Lmx1a) merge to control the expression of Nurr1. Nurr1 is an orphan nuclear receptor belonging to the NR4A subfamily, which comprises NR4A1, NR4A2, and NR4A3 (also known as Nur77, Nurr1, and Nor1, respectively) and critically regulates mDA neuron development and survival. Nurr1 knockout resulted in a loss of mDA neurons (Castillo, et al. Mol Cell Neurosci 11, 36-46 (1998); Saucedo-Cardenas, et al. Proc Natl Acad Sci USA 95, 4013-4018 (1998); Zetterström, et al. Science 276, 248-250 (1997)), indicating that Nurr1 plays an essential role for the development of mDA neurons. Notably, Nurr1 expression continues throughout adulthood, suggesting that its functional role is not limited to early development but extends into adulthood to maintain mDA neurons. Indeed, a recent study using conditional targeting strategy showed that Nurr1 ablation in the developing embryo or in fully differentiated adult neurons resulted in a loss of mDA neuron-specific gene expression and neuron degeneration (Kadkhodaei, et al. J Neurosci 29, 15923-15932 (2009)). As a master regulator, Nurr1 activates the expression of multiple genes involved in mDA neuronal phenotypes and survival such as the tyrosine hydroxylase (TH) gene, which is the first and rate-limiting step of DA biosynthesis, aromatic amino acid decarboxylase (AADC), dopamine transporter (DAT), vesicular monoamine transporter (VMAT), and Glial cell line-derived neurotrophic factor (GDNF) c-Ret kinase genes, which regulate the DA neurotransmitter phenotype and survival of mDA neurons (Smits, et al. Eur J Neurosci 18, 1731-1738 (2003); Wallen & Perlmann. Ann N Y Acad Sci 991, 48-60 (2003); Wallen, et al. Mol Cell Neurosci 18, 649-663 (2001)). These studies substantiate that Nurr1 plays an essential role in the development, maintenance and survival of mDA neurons. In fact, earlier studies revealed that the expression of Nurr1 is diminished in both aged and PD postmortem brain tissues (Chu, et al. Journal of Comparative Neurology 450, 203-214 (2002); Chu, et al. The Journal of comparative neurology 494, 495-514, (2006)). Also, functional mutations and polymorphisms of Nurr1 have been identified in rare cases of familial late-onset forms of PD although their biological significance remains elusive (Grimes, et al. Mov Disord 21, 906-909 (2006); Le, et al. Nature genetics 33, 85-89 (2003); Zheng, et al. Arch Neurol 60, 722-725 (2003)). Taken together, these data strongly suggest that the function of Nurr1 is critically related to the neurodegeneration of DA neurons and its activation may improve PD pathogenesis. Not only in PD, Nurr1 signalling is also implicated in other neurological conditions, such as Alzheimer's disease (Moon, et. al J Neurochem. 132, 254-62 (2015), schizophrenia, bipolar disorders and manic depression (Rojas, et. al Mol Psychiatry. 12, 756-66 (2007); Xing, et. al Schizophr Res. 84,36-56 (2006); Buervenich, et. al Am J Med Genet. 96, 808-13 (2000)). In addition, Nurr1's involvement has also been highlighted in non-neurological conditions such as cancer [Gou, et. al. Clin Transl Oncol 17, 788-794 (2015); Inamoto, et. al Cancer 116, 340-346 (2010); Mohan, et. al Clin Cancer Res 18, 3223-3228 (2012); Ranhotra, J Recept Signal Transduct Res. 35, 184-188 (2015); Smith, et. al Pigment Cell Melanoma Res. 24, 551-63 (2011); Llopis, et. al BMC Cancer 13, 139 (2013); Wang, et. al Asian Pac J Cancer Prev. 14, 2023-2028 (2013); Holla, et. al J Biol Chem. 281, 2676-2682 (2006)] and rheumatoid arthritis (McEvoy, et. al J Immun. 168, 2979-2987 (2002)), highlighting the importance of Nurr1 activation in various pathological conditions.

However, despite extensive attempts to identify natural and endogenous ligands, Nurr1 is still arguably an orphan nuclear receptor, because the identity of its natural and physiological ligands remains unknown.

Therefore, there is a considerable need to identify ligands of Nurr1 as well as compounds that can activate Nurr1 for use in the prevention or treatment of Parkinson's disease, as well as other neurological and non-neurological diseases involving dysregulated Nurr1.

SUMMARY OF THE INVENTION

The present invention satisfies the afore-mentioned need in the art by providing ligands and compounds that bind to and activate Nurr1.

In a first aspect, the invention relates to a crystalline form, wherein the form is a co-crystal comprising the Nuclear receptor related 1 protein-ligand binding domain (Nurr1-LBD) and a cyclopentenone prostaglandin.

In various embodiments, the Nurr1-LBD has the amino acid sequence set forth in SEQ ID NO:1.

In various embodiments, the cyclopentenone prostaglandin is selected from the group consisting of prostaglandin A1 (PGA1), prostaglandin A2 (PGA2), 15-deoxy-Δ12,14-prostaglandin J2 (15-d-Δ12,14-PGJ2), Δ12-Prostaglandin J2 (Δ12-PGJ2), and Prostaglandin J2 (PGJ2).

In preferred embodiments, Nurr1-LBD has the amino acid sequence set forth in SEQ ID NO:1, the cyclopentenone prostaglandin is PGA1, and the co-crystal is described by the atomic coordinates deposited at the Protein Data Bank (PDB) under accession number 5Y41.

In preferred embodiments, Nurr1-LBD has the amino acid sequence set forth in SEQ ID NO:1, the cyclopentenone prostaglandin is PGA2, and the co-crystal is described by the atomic coordinates deposited at the Protein Data Bank (PDB) under accession number 5YD6.

In a second aspect, the invention relates to a computer-assisted method for identifying or designing a compound that fits within or binds to Nurr1-LBD or a portion thereof, the method comprising the steps of:

a) providing the structure of Nurr1-LBD or a portion thereof as defined in the co-crystal described herein;

b) providing the structure of a candidate compound;

c) fitting the structure of the candidate compound to the structure of Nurr1-LBD or a portion thereof, wherein fitting comprises determining interactions between one or more atoms of the candidate compound and one or more atoms of Nurr1-LBD or a portion thereof to predict whether the candidate compound binds to or within Nurr1-LBD or a portion thereof; and d) selecting the candidate molecule if it is predicted to bind to or within Nurr1-LBD or a portion thereof.

In various embodiments, the structure of Nurr1-LBD is derived from the co-crystal structures of PDB ID No. 5Y41 and/or No. 5YD6.

In various embodiments, the candidate compound is selected from a virtual chemical library or is a cyclopentenone prostaglandin or a derivative thereof.

In a third aspect, the invention relates to a method of modulating, preferably activating, Nurr1, the method comprising contacting Nurr1 with an effective amount of a cyclopentenone prostaglandin or a derivative thereof or a compound identified or designed by the method described herein.

In a fourth aspect, the invention relates to a method of preventing or treating a disease, disorder, or condition associated with Nurr1 in a subject, the method comprising administering to said subject an effective amount of a cyclopentenone prostaglandin or a derivative thereof or a compound identified or designed by the method described herein.

In various embodiments, the subject is a mammal, preferably a human.

In various embodiments, the disease, disorder, or condition is selected from the group consisting of cancer, rheumatoid arthritis, Alzheimers, schizophrenia, manic depression, and Parkinson's disease, preferably Parkinson's disease.

In a fifth aspect, the invention relates to the use of a cyclopentenone prostaglandin or a derivative thereof or a compound identified or designed by the method described herein as a modulator, preferably activator, of Nurr1.

In a sixth aspect, the invention relates to the use of a cyclopentenone prostaglandin or a derivative thereof or a compound identified or designed by the method described herein as a medicament.

In preferred embodiments of all afore-described aspects of the invention, the cyclopentenone prostaglandin refers to PGA1 or PGA2.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
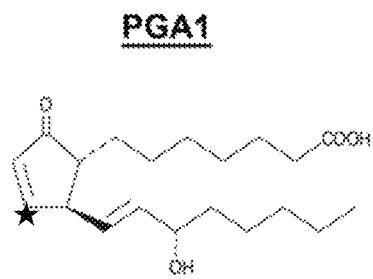
FIG. 1. Chemical structures cyPG's PGA1 and PGA2, the identified activators of Nurr1 which can covalently bind to Nurr1 (The C11 atom which can covalently attach by Michael addition is indicated by an *).
Figure 1:
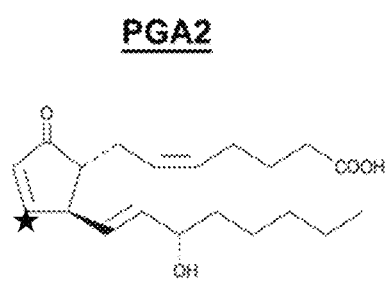

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

The present invention is based on the surprising finding of the inventors that PGA1 and PGA2 can bind to and activate Nurr1.

In a first aspect, the invention relates to a crystalline form, wherein the form is a co-crystal comprising the Nuclear receptor related 1 protein-ligand binding domain (Nurr1-LBD) and a cyclopentenone prostaglandin.

The term "crystalline form" as used herein refers to a crystalline solid comprising a given substance, including single-component crystal forms and multiple-component crystal forms, and including, but not limited to, polymorphs, solvates, hydrates, co-crystals and other molecular complexes, as well as salts, solvates of salts, hydrates of salts, other molecular complexes of salts, and polymorphs thereof.

In certain embodiments, a crystal form of a substance can be substantially free of amorphous forms and/or other crystal forms. In other embodiments, a crystal form of a substance can contain about 1%, about 2%, about 3%, about 4%, about 5%, about 10%, about 15%, about 20%, about 25%, about 30%, about 35%, about 40%, about 45% or about 50% of one or more amorphous form(s) and/or other crystal form(s) on a weight and/or molar basis. The term "co-crystal" as used herein refers to a crystalline form that contains more than one component in a crystal lattice. Co-crystals include crystalline molecular complexes of two or more molecules bound together in a crystal lattice through non-ionic interactions.

Certain crystal forms of a substance can be obtained by a number of methods, such as, without limitation, melt recrystallization, melt cooling, solvent recrystallization, recrystallization in confined spaces, such as, e.g., in nanopores or capillaries, recrystallization on surfaces or templates, such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, solvent-drop grinding, microwave-induced precipitation, sonication-induced precipitation, laser-induced precipitation, and/or precipitation from a supercritical fluid.

Techniques for characterizing crystal forms and amorphous forms can include, but are not limited to, thermal gravimetric analysis (TGA), differential scanning calorimetry (DSC), X-ray powder diffractometry (XRPD), single crystal X-ray diffractometry, vibrational spectroscopy, e.g., infrared (IR) and Raman spectroscopy, solid-state nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies.

The crystalline form of the present application is a co-crystal comprising Nurr1-LBD and a cyclopentenone prostaglandin. The Nurr1 may be of any species of origin, preferably one of the following:

| Species | NCBI Reference Sequence | Sequence ID |
|---|---|---|
| Homo sapiens | NP_006177.1 | SEQ ID NO: 3 |
| Mus musculus | NP_001132981.1 | SEQ ID NO: 4 |
| Rattus norvegicus | NP_062201.2 | SEQ ID NO: 5 |

The ligand binding domain of Nurr1, i.e. Nurr1-LBD, in the context of the present application refers to amino acids residues 328-598 of Nurr1 and is preferably any one of the following:

| Species | Amino acid sequence | Sequence ID |
|---|---|---|
| Homo sapiens | MVKEVVRTDSLKGRRGRLPSKPKSPQEPSP<br>PSPPVSLISALVRAHVDSNPAMTSLDYSRFQ<br>ANPDYQMSGDDTQHIQQFYDLLTGSMEIIRG<br>WAEKIPGFADLPKADQDLLFESAFLELFVLRL<br>AYRSNPVEGKLIFCNGVVLHRLQCVRGFGE<br>WIDSIVEFSSNLQNMNIDISAFSCIAALAMVTE<br>RHGLKEPKRVEELQNKIVNCLKDHVTFNNGG<br>LNRPNYLSKLLGKLPELRTLCTQGLQRIFYLK<br>LEDLVPPPAIIDKLFLDTLPF | SEQ ID NO: 1 |

-continued

| Species | Amino acid sequence | Sequence ID |
|---|---|---|
| *Mus musculus* or *Rattus norvegicus* | MVKEVVRTDSLKGRRGRLPSKPKSPQDPSP PSPPVSLISALVRAHVDSNPAMTSLDYSRFQ ANPDYQMSGDDTQHIQQFYDLLTGSMEIIRG WAEKIPGFADLPKADQDLLFESAFLELFVLRL AYRSNPVEGKLIFCNGVVLHRLQCVRGFGE WIDSIVEFSSNLQNMNIDISAFSCIAALAMVTE RHGLKEPKRVEELQNKIVNCLKDHVTFNNGG LNRPNYLSKLLGKLPELRTLCTQGLQRIFYLK LEDLVPPPAIIDKLFLDTLPF | SEQ ID NO: 2 |

The term "cyclopentenone prostaglandin" as used herein refers to a member of the subset of prostaglandins and prostanoids sharing a common mono-unsaturated cyclopentenone structure, preferably selected from the group consisting of prostaglandin A1 (PGA1), prostaglandin A2 (PGA2), 15-deoxy-Δ12,14-prostaglandin J2 (15-d-Δ12,14-PGJ2), Δ12-Prostaglandin J2 (Δ12-PGJ2), and Prostaglandin J2 (PGJ2).

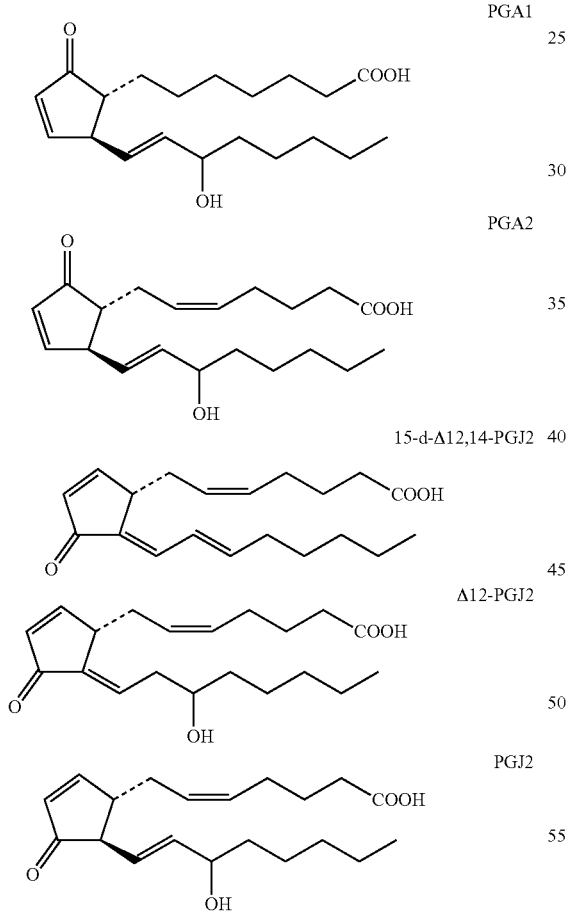

As the Nurr1 protein is highly conserved across species and the cyclopentenone prostaglandins are similar in structure, without wishing to be bound to any theory it is believed that the co-crystals of a Nurr1-LBD and a cyclopentenone prostaglandin share significant structural similarity.

In various embodiments, the Nurr1-LBD is of human origin and has the amino acid sequence set forth in SEQ ID NO:1.

In various embodiments, the cyclopentenone prostaglandin is selected from the group consisting of PGA1, PGA2, 15-d-Δ12,14-PGJ2, Δ12-PGJ2, and PGJ2.

In preferred embodiments, the Nurr1-LBD has the amino acid sequence set forth in SEQ ID NO:1, the cyclopentenone prostaglandin is prostaglandin A1 (PGA1), and the co-crystal is described by the atomic coordinates deposited at the Protein Data Bank (PDB) under accession number 5Y41.

In preferred embodiments, the Nurr1-LBD has the amino acid sequence set forth in SEQ ID NO:1, the cyclopentenone prostaglandin is prostaglandin A2 (PGA2), and the co-crystal is described by the atomic coordinates deposited at the Protein Data Bank (PDB) under accession number 5YD6.

Further encompassed in the present application is a process of crystallizing Nurr1-LBD and a cyclopentenone prostaglandin, whereby the afore-described co-crystals may be prepared. Said process comprises the steps of: (a) recombinantly expressing Nurr1-LBD, (b) purifying the recombinantly expressed Nurr1-LBD and (c) crystallizing the purified Nurr1-LBD.

In preferred embodiments, a) the human Nurr1-LBD construct coding for residues 328-598 (Nurr1-LBD) is cloned into a suitable expression vector which preferably encodes an affinity tag for the subsequent purification of Nurr1-LBD, e.g. the pETSUMO expression vector (LifeSensors, USA), and transformed into a suitable host bacterial cell, e.g. the BL21 (DE3) *E. coli*. Preferably, cells are grown till optical density at 600 nm reached 0.6-0.8 and then protein expression is induced by 1.0 mM Isopropyl β-D-1-thiogalactopyranoside (IPTG) for 4 h at 25° C., after which the cells are harvested and lysed by sonication, and/or b) purification is preferably accomplished using an affinity tag encoded by the expression vector. For example, it can be achieved using two rounds of $Ni^{2+}$-NTA, before and after SUMO tag cleavage if the pETSUMO expression vector is used, followed by gel filtration using HiLoad 16/60 Superdex 75 column (GE Healthcare, Sweden), and/or c) purified Nurr1-LBD in 50 mM Tris pH 8.0, 150 mM NaCl is concentrated to 10-12 mg/ml and incubated overnight with Prostaglandin A1 (PGA1) or Prostaglandin A2 (PGA2) at 1:4 molar ratio for crystallization using the 24-well 'Linbro' style hanging drop vapor diffusion crystal growth plate. Crystals are obtained with a 1 mL well-solution constituting 20% PEG 3350, 0.1 M MES pH 5.5-6.5 and 0.2 M $MgCl_2$. The drop-solution is made up of 2 μL Nurr1-LBD-PGA1/PGA2 solution and 2 μL well-solution. The PEG molecular weight could vary from 100 up to 8000. The MES buffer could be substituted by Bis Tris pH 5.8-6.5, or any buffer with pH range of 5.0 up to 7.0. The buffer concentration could vary from 0.05M up to 0.5M. In addition, the drop:well ratio could vary from 20 nL up to 100 μL.

It should be noted that a solution comprising recombinant Nurr1-LBD protein and a cyclopentenone prostaglandin, which may be used for the crystallization process, is also within the scope of the present application.

In a second aspect, the invention relates to a computer-assisted method for identifying or designing a compound that fits within or binds to Nurr1-LBD or a portion thereof, the method comprising the steps of:

a) providing the structure of Nurr1-LBD or a portion thereof as defined in the co-crystal described herein;

b) providing the structure of a candidate compound;

c) fitting the structure of the candidate compound to the structure of Nurr1-LBD or a portion thereof, wherein fitting comprises determining interactions between one or more atoms of the candidate compound and one or more atoms of Nurr1-LBD or a portion thereof to predict whether the candidate compound binds to or within Nurr1-LBD or a portion thereof; and d) selecting the candidate molecule if it is predicted to bind to or within Nurr1-LBD or a portion thereof.

The structural information suitable for the practice of the present application shall include atomic coordinate data of Nurr1-LBD, and lists each atom by a unique number; the chemical element and its position for each amino acid residue, the amino acid residue in which the element is located, the chain identifier, the number of the residue, coordinates (e.g., X, Y, Z) which define with respect to the crystallographic axes the atomic position (in angstroms) of the respective atom, the occupancy of the atom in the respective position, isotropic displacement parameter (in angstroms) which accounts for movement of the atom around its atomic center, and atomic number. Nurr1-LBD structure can be obtained by removing other molecules, e.g. PGA1 or PGA2, from the co-crystal structures described above.

For identifying Nurr1 modulators (activators or inhibitors), structural information of the native Nurr1-LBD could not be used, as the binding pocket is concealed. In this regard, it is advantageous to utilize structural information from one or more co-crystals of the Nurr1-LBD with one or more binding compounds. In various embodiments, the coordinates of Nurr1-LBD are derived from the PDB ID No. 5Y41 and/or No. 5YD6.

The co-crystals of the invention, and particularly the atomic structure coordinates of the Nurr1-LBD obtained therefrom, have a wide variety of uses. The co-crystals and structure coordinates are particularly useful for identifying compounds that bind to Nurr1-LBD. The provision of the crystal structure of Nurr1-LBD complexed with a cyclopentenone prostaglandin provides the skilled artisan with a structure-based approach to design or screen for compounds that bind to Nurr1-LBD.

Structure-based compound design and identification methods are powerful techniques that can involve searching virtual chemical libraries (i.e. computer databases) containing a wide variety of potential modulators and chemical functional groups and fitting them into the active site or putative binding site of the protein structure. The term "fitting" as used herein can mean determining, by automatic or semi-automatic means, interactions between at least one atom of the candidate compound and at least one atom of the Nurr1-LBD and calculating the extent to which such an interaction is stable. Interactions can include attraction, repulsion, brought about by charge, steric considerations, and the like. The computerized design and identification of modulators is useful as the virtual chemical libraries contain more compounds than the real chemical libraries, often by an order of magnitude. For reviews of structure-based drug design and identification (see Kuntz et al. (1994), Acc. Chem. Res. 27:117; Guida (1994) Current Opinion in Struc. Biol. 4: 777; Colman (1994) Current Opinion in Struc. Biol. 4: 868).

One method of rational design searches for modulators by docking the computer representations of compounds from a virtual chemical library. Publicly available virtual chemical libraries include, with limitation, the following:

(a) ACD from Molecular Designs Limited;
(b) NCI from National Cancer Institute;
(c) CCDC from Cambridge Crystallographic Data Center;
(d) CAST from Chemical Abstract Service;
(e) Derwent from Derwent Information Limited;
(f) Maybridge from Maybridge Chemical Company LTD;
(g) Aldrich from Aldrich Chemical Company; and/or
(h) Directory of Natural Products from Chapman & Hall.

One such virtual chemical library (e.g. ACD) contains compounds that are synthetically derived or are natural products. Methods available to those skilled in the art can convert a data set represented in two dimensions to one represented in three dimensions. These methods are enabled by such computer programs as CONCORD from Tripos Associates or DE-Converter from Molecular Simulations Limited.

Multiple methods of structure-based modulator design are known to those in the art (Kuntz et al., (1982), J. Mol. Biol. 162: 269; Kuntz et aZ., (1994), Acc. Chern. Res. 27:117; Meng et al., (1992), J. Compt. Chem. 13:505; Bohm, (1994), J. Comp. Aided Molec. Design 8: 623).

A computer program widely utilized by those skilled in the art of rational modulator design is DOCK from the University of California in San Francisco. The general methods utilized by this computer program and programs like it are described below. More detailed information regarding some of these techniques can be found in the Accelerys User Guide, 1995. A typical computer program used for this purpose can perform a process comprising the following steps or functions:

(a) removing the existing compound from the protein;
(b) docking the structure of another compound into the active-site or putative binding site using the computer program (such as DOCK) or by interactively moving the compound into the active-site or putative binding site;
(c) characterizing the space between the compound and the atoms of the active-site or putative binding site;
(d) searching libraries for (i) compounds can fit into the empty space between the compound and the active-site or putative binding site, or (ii) molecular fragments which can be assembled to generate a candidate compound for further evaluation.

Part (c) refers to characterizing the geometry and the complementary interactions formed between the atoms of the active site or putative binding site and the compounds. A favorable geometric fit is attained when a significant surface area is shared between the compound and active-site atoms without forming unfavorable steric interactions. One skilled in the art would note that the method can be performed by skipping part (d) and screening a database of many compounds.

Other methods of structure-based modulator design are reported in the literature and can be used, e.g.:

(1) CAVEAT: Bartlett et al., (1989), in Chemical and Biological Problems in Molecular Recognition, Roberts, S. M.; Ley, S. V.; Campbell, M. M. eds.; Royal Society of Chemistry: Cambridge, pp. 182-196.

(2) FLOG: Miller et al., (1994), J. Comp. Aided Molec. Design 8:153.

(3) PRO Modulator: Clark et al., (1995), J. Comp. Aided Molec. Design 9:13.

(4) MCSS: Miranker and Karplus, (1991), Proteins: Structure, Function, and Genetics 11:29.

(5) AUTODOCK: Goodsell and Olson, (1990), Proteins: Structure, Function, and Genetics 8:195.

(6) GRID: Goodford, (1985), J. Med. Chem. 28:849.

Another way of identifying compounds as potential modulators is to modify an existing modulator. For example, the computer representation of modulators can be modified within the computer representation of a cyclopentenone prostaglandin or a derivative thereof, PGA1 or PGA2 in particular. Detailed instructions for this technique can be found, for example, in the Accelerys User Manual, 1995 in LUDI. The computer representation of the modulator is typically modified by the deletion of a chemical group or groups or by the addition of a chemical group or groups.

In preferred embodiments, the candidate compound is a cyclopentenone prostaglandin or a derivative thereof. The term "derivative" as used herein refers to a chemical substance related structurally to a parent compound, i.e., a cyclopentenone prostaglandin. A derivative in the context of the present application comprises the same basic carbon skeleton and functionality as the parent compound, but can also bear one or more substituents or substitutions of the parent compound.

Upon each modification to the compound, the atoms of the modified compound and active site or putative binding site can be shifted in conformation and the distance between the modulator and the active-site atoms may be scored along with any complementary interactions formed between the two molecules. Scoring can be complete when a favorable geometric fit and favorable complementary interactions are attained. Compounds that have favorable scores are potential modulators.

Without wishing to be bound to any theory, it is believed that the potential modulators may couple covalently to Nurr1, preferably to the amino acid residue Cys566 of Nurr1. Alternatively, the potential modulators may interact with Nurr1 noncovalently, preferably interacting with one or more amino acid residues selected from the group consisting of Glu440, Ser441, Phe443, Leu444, Arg515, His516, Cys566, Arg563, Leu570, Ile573, Thr567, Leu591, Thr595, and Pro597.

Accordingly, provided herein is a computer-based method of virtual screening and/or rational design of Nurr1-LBD binders or modulators, which can be used in conjunction with "wet" assay screening. As large virtual chemical libraries of compounds can be searched in a matter of hours or even less, the computer-based method can narrow the compounds tested as potential modulators of Nurr1 function in biochemical or cellular assays (e.g. luciferase reporter assay).

In a third aspect, the invention relates to a method of modulating, preferably activating, Nurr1, the method comprising contacting Nurr1 with an effective amount of a cyclopentenone prostaglandin or a derivative thereof or a compound identified or designed by the method described herein (e.g. the derivative YH279 described in Example 6).

This method may be carried out in vitro, ex vivo, or in vivo.

In preferred embodiments, the cyclopentenone prostaglandin is PGA1 or PGA2.

In a fourth aspect, the invention relates to a method of preventing or treating a disease, disorder, or condition associated with Nurr1 in a subject, the method comprising administering to said subject an effective amount of a cyclopentenone prostaglandin or a derivative thereof or a compound identified by the method described herein (e.g. the derivative YH279 described in Example 6), preferably PGA1 or PGA2 or a derivative thereof. Alternatively, the invention also covers the use of said compound for the manufacture of a medicament for the treatment or prevention of a disease, disorder, or condition.

The term "subject" is used interchangeably with "individual" and "patient" herein and refers to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The disease, disorder, or condition may be any one associated with Nurr1 signaling, preferably selected from the group consisting of cancer, rheumatoid arthritis, Alzheimers disease, schizophrenia, manic depression and Parkinson's disease, more preferably Parkinson's disease.

Other neurodegenerative diseases that may be treated with a compound or method described herein include Alexander's disease, Alper's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes *dorsalis*.

By the terms "effective amount" and "therapeutically effective amount" of a compound of the invention is meant a nontoxic but sufficient amount of said compound to provide the desired effect.

A compound of the present invention may be administered in the form of a salt, ester, amide, prodrug, active metabolite, analog, or the like, provided that the salt, ester, amide, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992). "Pharmacologically active" (or simply "active") as in a "pharmacologically active" derivative or analog, refers to a derivative or analog having the same type of pharmacological activity as the parent compound and approximately equivalent in degree.

Prior to being used in the treatment in vivo, pharmaceutical formulations composed of the compound in association with a pharmaceutically acceptable carrier may need to be formulated. See Remington: *The Science and Practice of Pharmacy*, 19th Ed. (Easton, Pa.: Mack Publishing Co., 1995), which discloses typical carriers and conventional methods of preparing pharmaceutical formulations.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy, cited above.

The compound of the present invention may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the compound administered will, of course, be dependent on the particular active agent, the condition or disorder being treated, the severity of the condition or disorder, the subject's weight, the mode of administration and other pertinent factors known to the prescribing physician.

In a fifth aspect, the invention relates to the use of a cyclopentenone prostaglandin or a derivative thereof or a compound identified or designed by the method described herein (e.g. the derivative YH279 described in Example 6), preferably PGA1 or PGA2, as a modulator, preferably activator, of Nurr1.

In a sixth aspect, the invention relates to the use of a cyclopentenone prostaglandin or a derivative thereof or a compound identified or designed by the method described herein (e.g. the derivative YH279 described in Example 6), preferably PGA1 or PGA2, as a medicament.

The present invention is further illustrated by the following examples. However, it should be understood, that the invention is not limited to the exemplified embodiments.

EXAMPLES

Materials and Methods
Protein Expression, Purification, Crystallization and Structure Determination The human Nurr1-LBD construct coding for residues 328-598 (hNurr1-LBD) was cloned into pETSUMO expression vector (LifeSensors, USA) and transformed in BL21 (DE3) *E. coli*. Cells were grown till optical density at 600 nm reached 0.6-0.8 and then protein expression was induced by 1.0 mM Isopropyl β-D-1-thiogalactopyranoside (IPTG) for 4 h at 25° C., after which the cells were harvested and lysed by sonication. Purification was carried out using two rounds of $Ni^{2+}$-NTA, before and after SUMO tag cleavage, followed by gel filtration using HiLoad 16/60 Superdex 75 column (GE Healthcare, Sweden). Purified Nurr1-LBD in 50 mM Tris pH 8.0, 150 mM NaCl was concentrated to 10 mg/ml and incubated overnight with Prostaglandin A1 (PGA1) (SantaCruz Biotechnology, USA) at 1:4 molar ratio for crystallization. Crystals could be obtained using the hanging drop vapor diffusion with 20% PEG 3350, 0.1 M MES pH 5.5 and 0.2 M $MgCl_2$. X-ray data collection was carried out at 100 K on beamline X06DA at the Swiss Light Source (Villigen, Switzerland) and beamline 13B1 at the Taiwan Light Source (Hsinchu, Taiwan), with 20% ethylene glycol as the cryo protectant supplemented to the reservoir solution. The best data could be obtained from a Nurr1-LBD-PGA1 and Nurr1-LBD-PGA2 co-crystal which diffracted to 2.05 Å and 2.34 Å, respectively. The data was indexed, integrated, merged and scaled using the software iMosflm (Battye, et al. Acta Crystallogr D Biol Crystallogr 67, 271-281 (2011)) and SCALA (Evans, Acta Crystallogr D Biol Crystallogr 62, 72-82 (2006)) from CCP4 suite of programs (Winn, et al. Acta Crystallogr D Biol Crystallogr 67, 235-242 (2011)). The co-crystals of Nurr1-LBD in complex with PGA1 and PGA2 belonged to the orthorhombic space groups $P2_12_12$ and $P2_12_12_1$ with two and four molecules in the asymmetric unit, respectively. Phasing by molecular replacement using PHASER (McCoy, et. al. J Appl Crystallogr 40, 658-674 (2007)) with apo Nurr1-LBD structure (PDB ID 1OVL) (Wang, et. al Nature 423, 555-560 (2003)) was used as the search model. REFMAC (Murshudov, et. al Acta Crystallogr D Biol Crystallogr 67, 355-367 (2011)) and COOT (Emsley, et. al Acta Crystallogr D Biol Crystallogr 60, 2126-2132 (2004)) were used for refinement and map fitting respectively. The electron density indicated re-orientation of the H12 helix, which was manually traced and modelled into the electron density map. After this the electron density for the PGA1/PGA2 molecule could be unequivocally observed packed mainly by H12, H4 and H11 helices. Water molecules were manually picked from the Fo-Fc and 2Fo-Fc electron density map contoured at 3.0 and 1.0σ cut-offs, respectively. Two PEG molecules and a magnesium ion, from the crystallization solution, trapped in the monomer interfaces were also observed during map fitting.

Nuclear Magnetic Resonance (NMR) Data Collection and Analysis 0.2 mM uniformly $^{15}$-N labeled Nurr1-LBD protein was prepared in 20 mM sodium phosphate buffer containing 50 mM NaCl, 0.01% $NaN_3$ (pH 7.5) in 90% $H_2O$/10% $D_2O$. The interaction between Nurr1-LBD and PGA1/PGA2 (in DMSO vehicle) was examined using two dimensional HSQC comparing free protein sample with 1:10 molar ratio of Nurr1-LBD:PGA1/PGA2. The backbone resonance and sequence specific resonance assignments were previously assigned for Nurr1-LBD as reported (Kim, et. al. Proc Nat Acad Sci 112, 8756-8761 (2015)). The binding sites of PGA1/PGA2 were mapped on the crystal structure of Nurr1-LBD (PDB code: 1OVL) after determining the chemical shift perturbations following the addition of PGA1/PGA2 against the spectrum of the free protein. Bruker Avance II 700 MHz spectrometer fitted with a 5 mm triple resonance, z-axis-gradient cryoprobe at 298K was used for all NMR experiments. All spectra were processed directly to SPARKY format in UNIX and analyzed using the SPARKY 3.114 program (Goddard and Kneller, SPARKY In, 3.114 Edition: Univ of Calif (2002)).

Top-Down Mass Spectrometry

Nurr1-LBD at ~300 μM prepared in 0.1% FA in water was analyzed using a Dionex UltiMate 3000 UHPLC coupled to a linear quadrupole ion trap-Fourier transform Ultra apparatus (LTQ-FT Ultra, Thermo Scientific Inc.). Protein solution (5 μL) was injected directly into the detector carried by 0.1% FA in water at 500 μL/min. On-line ionization was performed using a Michrom CaptiveSpray ion source (Bruker-Michrom Inc., Auburn, USA) at an electrospray potential of 1.5 kV and capillary temperature of 200° C.

Data acquisition was conducted in profile and positive mode (600-1600 m/z range). Mass spectrometry (MS) data was acquired for 60 min in the FT-ICR cell at a resolution of 100,000 (at 400 m/z) and maximum injection time of 500 msec using Xcalibur version 2.0 SR2 (Thermo Scientific Inc., Bremen, Germany). The automatic gain control target for FT-ICR was set to 5.0e+05. For each scan 100 microscans were averaged. Peak deconvolution was performed with Xtract software (Thermo Scientific Inc., Bremen, Germany) with a S/N threshold of 5 and a fit factor of 44%. A similar protocol was adopted for Nurr1-LBD incubated with Prostaglandin A1 (PGA1)/Prostaglandin A2 (PGA2) overnight at 1:1.5 molar ratio.

Luciferase Assay $7.5 \times 10^3$ HEK293T (human embryonic kidney) cells/well were seeded into a 96-well white plate (Greiner, Austria). After 24 hours, the cells were transfected with pcDNA 3.1 Myc/His mouse full-length Nurr1 (gifted by Prof. Kwang-Soo Kim), pGL3-basic containing the canonical NBRE element (AAAGGTCA) and pRL-null vector (gifted by Prof. Valerie Lin) in the ratio of 3:3:4 to a total of 1 µg using X-tremeGENE HP DNA transfection reagent (Roche, Basel). The plasmids were first added into OPTI-MEM media (Gibco, CA) before the transfection reagent was carefully added and this reaction mix was incubated at room temperature for 15 minutes. In the 96-well plate, 100 µl of fresh DMEM media (Hyclone, CA) was infused into the well and 10 µl from the reaction mix containing the DNA and transfection reagent complex was added drop-wise to each well. The plate was gently tapped for 1-2 minutes before incubation for 24 hours at 37° C. in a 5% $CO_2$ humidified incubator. Following a change of fresh media 24 hours post-transfection, PGA1 or PGA2 was added accordingly into assigned wells at a 100-fold dilution. Luciferase reporter assay was carried out using the Dual-Luciferase® kit from Promega (Madison, WI). Briefly, in each sample well containing 20 µl of lysed cells, 100 µl of Luciferase Assay Reagent II was added into each well and the measurement was set with a 2-second delay followed by a 10-second integrated measurement period. After this measurement, 100 µl of Stop & Glo® reagent was added into each well before initiating the same measurement parameters. Luminescence readings were measured using either Tecan Infinite® 200 Pro or Tecan Safire² microplate readers (Männedorf, Switzerland). After obtaining sample measurements, each well measurement was subtracted from the average reading obtained after five measurements of the well containing non-transfected cells. Normalized Δfold activity of each sample was calculated using the following equation: Average (Firefly/*Renilla*) from sample/Average (Firefly/*Renilla*) from cells treated with DMSO vehicle (Promega).

Example 1: Cyclopentenone Prostaglandins Bind to Nurr1-LBD

In an earlier high throughput screening study of >340,000 compounds, a single hit, 6-mercaptopurine, was identified and shown to activate Nurr1 through a region in the amino terminus lacking a LBD (Ordentlich, Yan, Zhou & Heyman. Journal of Biological Chemistry 278, 24791-24799 (2003)). Another study from Novartis reported the identification of a novel class of compound that can activate Nurr1 approximately 2-fold compared to control (Hintermann. et al. Bioorganic & Medicinal Chemistry Letters 17, 193-196 (2007)). However, it is not known whether any of these compounds can directly interact with Nurr1's LBD. To the knowledge of the inventors of the present application, to date no small molecule has been identified that can modulate Nurr1 function through direct interaction with its LBD at canonical ligand-binding site. Two groups recently reported the identification of compounds that can activate Nur77, a NR4A2 receptor family member via its LBD (Chintharlapalli et al. J Biol Chem 280, 24903-24914 (2005); Zhan, et al. Nat Chem Biol 4, 548-556 (2008)). Furthermore, a novel interface has been identified on the Nurr1 LBD that could interact with co-activators/agonists (Codina, et al. J Biol Chem 279, 53338-53345 (2004)). Thus, it remains an open question whether small molecules could be identified, which can activate Nurr1 through the LBD. A recent study identified Nurr1 agonists sharing an identical chemical scaffold, 4-amino-7-chloroquinoline, suggesting a critical structure-activity relationship (Kim, et al. Proceedings of the National Academy of Sciences 112, 8756-8761 (2015)). The inventors found that two antimalarial drugs, amodiaquine (AQ) and chloroquine (CQ) enhance the transcriptional function of Nurr1 by binding with Nurr1-LBD at its non-canonical ligand-binding site (Kim, et al. Proceedings of the National Academy of Sciences 112, 8756-8761 (2015)).

Figure 2:
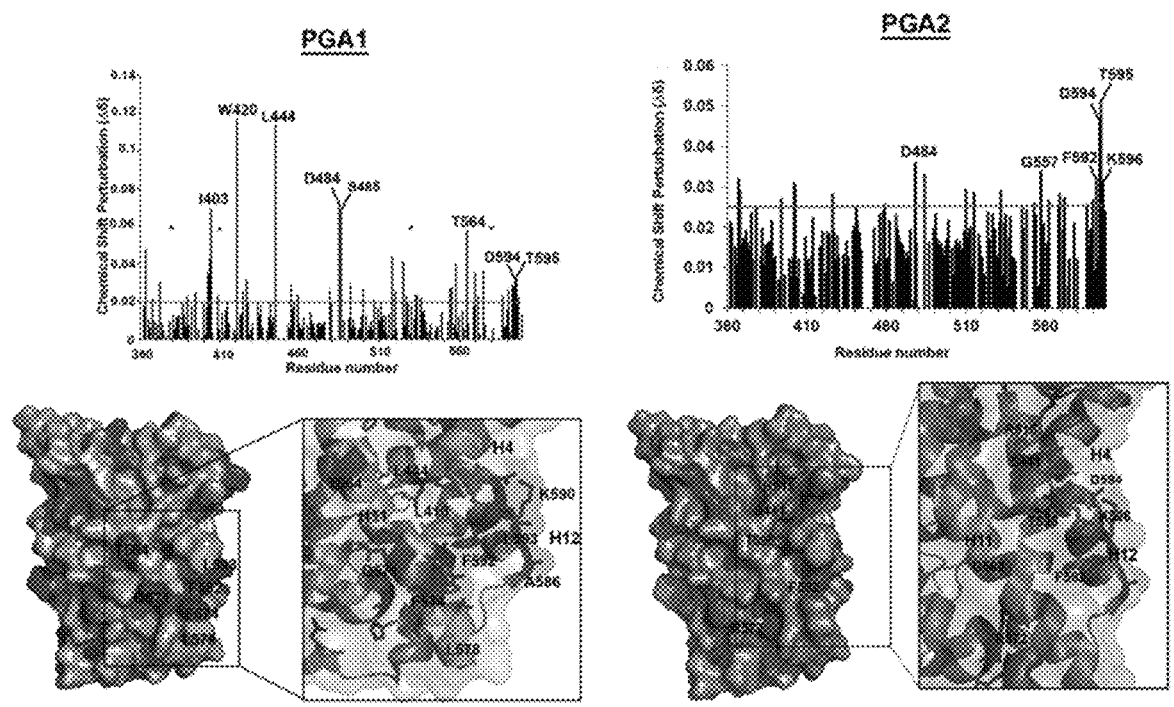
FIG. 2. 2D $^1$H-$^{15}$N HSQC experiment on Nurr1-LBD with cyPGs. The Chemical shift perturbation (CSP) plot of PGA1 (Left) and PGA2 (Right) binding to Nurr1-LBD, revealing residues with perturbed resonances. The CSP for each assigned amino acid residue may be derived as previously described. Notable Nurr1-LBD residues that gets perturbed are indicated for the respective cyPG's. The grey line marks the threshold used for mapping of the residues on the protein. Mapping of perturbed residues on crystal structure of Nurr1-LBD (PDB: 1OVL) with a close-up section showing affected helices H12, H4 and H11 with amino acid residues indicated. Residues highlighted in red denotes Δδ>0.025.

Prostaglandins are a family of biologically potent lipids from membrane phospholipids; comprised of a C20-unsaturated fatty acid containing a cyclopentenone ring. Prostaglandins have pleiotropic actions in CNS cells that differently affect the progress of inflammation and neuronal death or survival (Lima, Bastos, Limborco-Filho, Fiebich, & de Oliveira. Mediators of inflammation 2012, 946813 (2012)). While oxidized and unsaturated fatty acids were suggested to be a natural ligand of PPARγ and Nurr1 (Hughes, et al. Nature communications 5, 3571, doi:10.1038/ncomms4571 (2014); Itoh, et al. Nature structural & molecular biology 15, 924-931 (2008); de Vera, et al. ACS chemical biology (2016)), respectively, the inventors' continued screening attempt for endogenous Nurr1 ligands has led to the identification of cyclopentenone prostaglandins as potential natural ligands. Previous studies showed that PGA2, a cyclopentenone, directly interacts with mitochondria and induce intrinsic apoptosis in HL60 cells (Lee, et al. Prostaglandins & other lipid mediators 91, 30-37 (2010)), cause cell cycle arrest at G1 phase (Hitomi, et al. J Biol Chem 271, 9376-9383 (1996)) and shows antitumor and antiviral effects (Fukushima. et al. Advances in prostaglandin, thromboxane, and leukotriene research 19, 415-418 (1989); Marini, et al. British journal of cancer 61, 394-399 (1990)). PGA1 and A2 have been suggested to be formed by the dehydration in vitro, and is believed to be formed via PGE1 and E2 in vivo (Musiek et al. Brain pathology 15, 149-158 (2005)), respectively. Biological roles of the cyclopentenone prostaglandins in neuronal cells and neurodegenerative disorder remain elusive. In the studies to confirm if PGA1 and A2 directly binds to Nurr1-LBD, the inventors first examined the molecular interaction between PGA1 and PGA2 (FIG. 1) with Nurr1-LBD by employing NMR spectroscopy (FIG. 2). For this, the inventors prepared 15N-labeled Nurr1-LBD and then examined the chemical shift perturbations on a 2D 1H-15N HSQC spectra before and after the addition of these PGs. Chemical shift perturbations were observed from residues located in helix 11 and 12 of the ligand-binding domain the presence of PGs, confirming direct physical interaction between these PGs and Nurr1-LBD.

Example 2: Cyclopentenone Prostaglandins Activate Nurr1-Mediated Transcription

Figure 3:
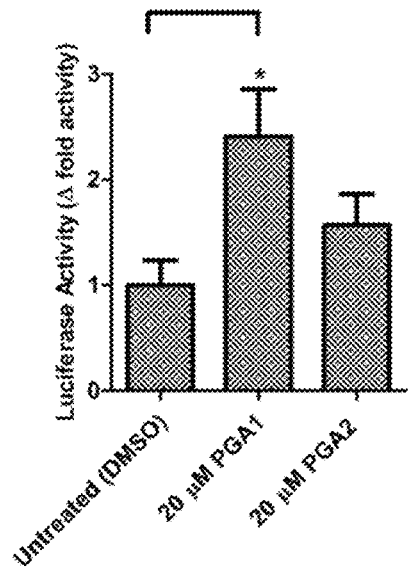
FIG. 3. CyPGs-mediated transcriptional activation of Nurr1. To confirm the in vitro binding results of the two cyPGs (PGA1 and PGA2) as Nurr1 ligand, a Nurr1-based luciferase reporter assay system was employed, showing that these two cyPGs potentiate Nurr1-LBD's transcriptional activation ability in human HEK293T cells. Results represent mean±SEM of luciferase activity from duplicate readings. Student's t-test (unpaired) was conducted to determine statistical significance between untreated and treated cells: *p<0.05.

The inventors' data revealed that PGs directly bind to Nurr1-LBD. To investigate whether cyclopentenone prostaglandins can activate Nurr1 function, luciferase reporter assay was performed to determine Nurr1's transcriptional activity following transfection of expression, luciferase reporter and control vectors and subsequently, drug treatment with PGA1 and PGA2, using HEK293T cells. Notably, PGA1 and PGA2 were able to stimulate Nurr1-dependent transcriptional activity up to 2.5-fold (FIG. 3).

Example 3: Cyclopentenone Prostaglandins Ameliorates Locomotor Deficits and Early Mortality in LRRK2 G2019S *Drosophila*

Figure 4:
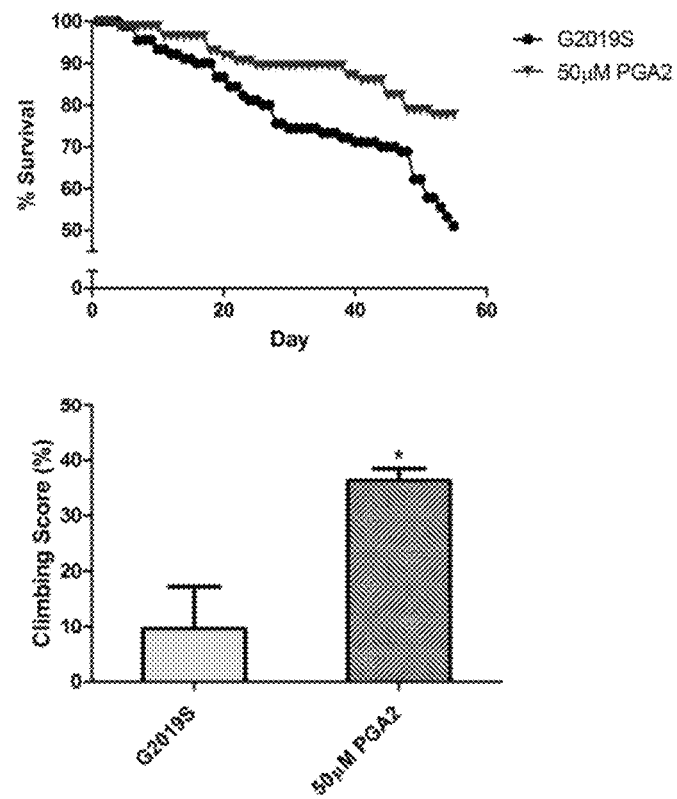
FIG. 4. Mitigation of locomotor deficits and mortality in LRRK2 G2019S Drosophila by CyPGs. Drosophila melanogaster expressing LRRK2 G2019S mutation driven by ddc-Gal4 result in late-onset PD in these flies. Treatment with 50 μM PGA2 was able to improve their climbing ability from 9.7% to 36.4% when compared to age-matched mutant flies (0.5% EtOH drug vehicle). Survival rate was determined by counting the number of flies that survived every 2-3 days for 55 days post-eclosion. Flies were treated with cornmeal-agar medium containing 50 μM PGA2 for 25 days at day 30 post-eclosion and climbing assay was carried out on day 55. The number of flies that climbed beyond a median line in a vertical column (length 25 cm; diameter 1.5 cm) were counted after one minute for an average of six times. Results represent mean±SEM of climbing scores from three independent experiments. Student's t-test (unpaired) was conducted to determine statistical significance between G2019S (vehicle treated) and PGA2-treated mutant flies: *p<0.05.

Flies expressing Leucine-rich repeat kinase 2 (LRRK2) with G2019S mutation driven by dopa decarboxylase (ddc)-Gal4 leads to late-onset PD in these flies (Liu, et al. Proc Natl Acad Sci USA 105, 2693-2698, doi:10.1073/pnas.0708452105 (2008)). Aged LRRK2 G2019S flies show severe loss of DA neurons, poorer climbing ability and early mortality (Liu, et al. (2008) Proceedings of the National Academy of Sciences, 105(7), pp. 2693-2698; Ng, et al. (2009) Journal of Neuroscience, 29(36), pp. 11257-11262). Treatment with PGA2 was able to rescue their climbing ability from 9.7% to 36.4% when compared to age-matched mutant flies and there was also improvement to their overall survival rate for PGA2 treated flies as compared to mutant flies (vehicle treated) (FIG. 4).

Example 4: Co-Crystallization of Nurr1-LBD in Complex with PGs

In humans, there are 48 known nuclear receptors (NRs). As intracellular proteins, they play critical roles in relaying extracellular signals to control the expression of genes involved in the development and metabolism of an organism. The structural organization of NRs is defined by 5-6 domains, denoted A-F from the N- to C-terminal. So far, the DNA-binding domain (DBD; denoted C) and Ligand-binding domain (LBD) have been well characterized and are highly conserved domains while the other regions are poorly conserved and highly variable (Germain, et al. Pharmacological reviews 58, 685-704 (2006)). Typically, NRs are activated upon ligand binding to its LBD which triggers recognition of specific target DNA sequences known as hormone response elements via its DBD. However, not all NRs have a cognate ligand which led to the naming of this group of NRs as orphan nuclear receptors. Nurr1 (NR4A2; nuclear receptor subfamily 4, group A, member 2) is an orphan nuclear receptor and transcription factor which was first identified in 1992, found to be highly expressed in the brain (Law, et al. Molecular Endocrinology 6, 2129-2135 (1992)). The functional domain organization of Nurr1 follows that of classical NRs and consists of two transactivation domains known as Activation Function-1 (AF-1) and Activation Function-2 (AF-2) at the N- and C-termini, respectively, with LBD at the C-terminal while the DBD is located in between the N- and C-termini. The highly conserved DBD consists of two zinc finger motifs and is able to recognize and interact with specific hormone response elements such as nerve growth factor-induced B (NGFI-B) response element (NBRE) as monomers or homodimers (Paulsen, et al. Journal of molecular neuroscience: MN 6, 249-255 (1995); Maira, et al. Molecular and cellular biology 19, 7549-7557 (1999)); Nur-response element (NurRE) as homodimers or NR4A heterodimers (Forman, et al. Annals of the New York Academy of Sciences 761, 29-37); or to DR5 motif with other nuclear receptors such as retinoid X receptor (RXR) (Perlmann & Jansson. Genes & development 9, 769-782 (1995); Zetterstrom, et al. Molecular endocrinology (Baltimore, Md.) 10, 1656-1666, doi:10.1210/mend.10.12.8961274 (1996)). A closer look at the crystal structure of Nurr1-LBD (Wang, et al. Nature 423, 555-560 (2003)) revealed that the folded tertiary structure of the LBD in the absence of any ligand is similar to the tertiary structures of other ligand-bound NR LBDs. However, interestingly it lacks a cavity for conventional ligand binding, suggesting that Nurr1 might be one of ligand-independent transcription factors.

Based on numerous studies indicating the critical and unique functional roles of Nurr1, intensive efforts have been made to identify potential agonists that can activate its function and have the potential to delay or prevent the onset of PD symptoms. Although members of the NR4A subgroup belong to classical nuclear receptors (NRs) with a potential LBD, endogenous/native ligands have not been identified till-date and thus have been designated as orphan NRs (Pearen & Muscat. Molecular endocrinology (Baltimore, Md.) 24, 1891-1903 (2010)).

Figure 5:
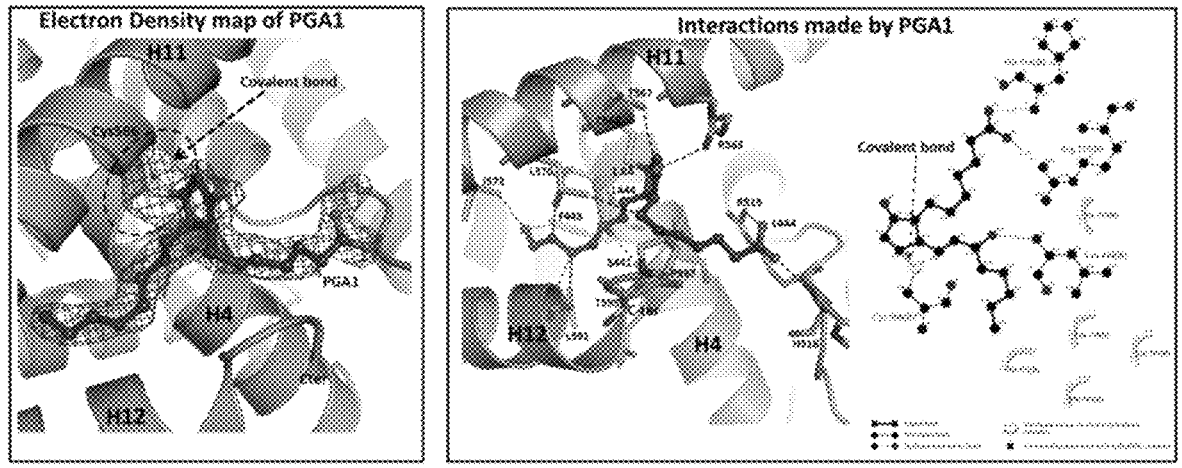
FIG. 5: The electron density and interactions of PGA1 (a) and PGA2 (b). The 2Fo-Fc electron density map of PGA1 (a) and PGA2 (b) contoured at 1a cut-off clearly revealing the covalent bond between the side-chain sulphur of Cys566 and C11 of PGA1/PGA2. The interactions made by PGA1 (a) and PGA2 (b), docked between helices H4, H11 and H12, with the Nurr1 residues mainly by hydrophobic contacts and a few hydrogen bonds, are also represented.
Figure 5:
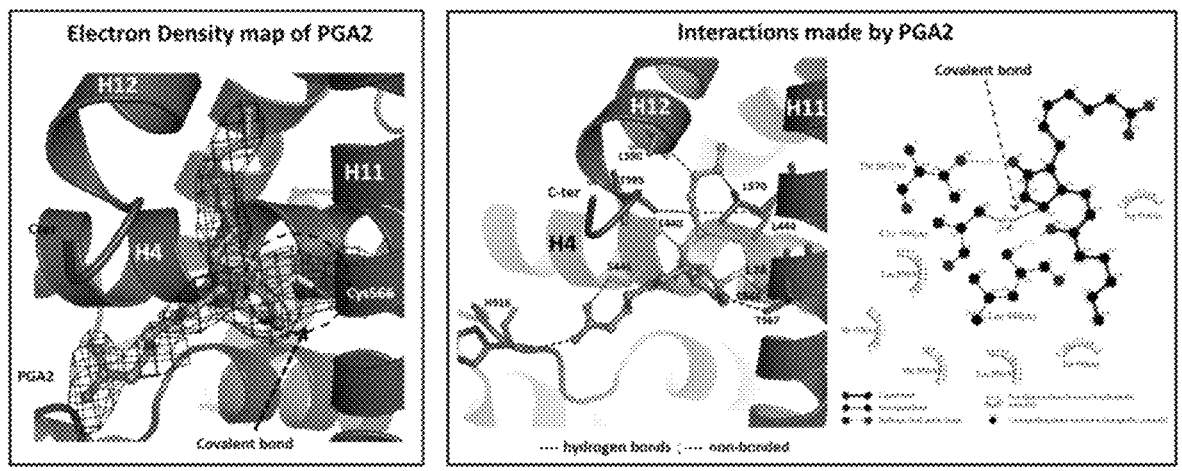
Figure 6:
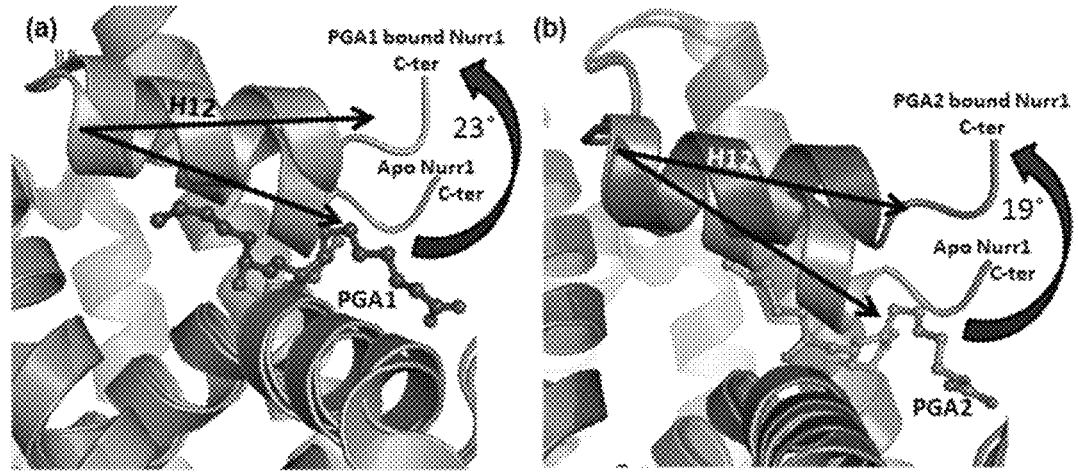
FIG. 6: A structural comparison of Nurr1-LBD complexes of PGA1 (Left) and PGA2 (Right) with its apo form. (Left) A superposition of the PGA1-bound Nurr1 with its apo form clearly shows a shift of the helix H12 by 23° away from the protein core, enabling the binding of PGA1 (ball and stick mode). (Right) A similar H12 shift of ~19° was observed from the superposition of the PGA2-bound Nurr1 with its apo form enabling the binding of PGA2 (ball and stick mode).

To better define underlying molecular basis of Nurr1 in recognizing PGs, in this study attempts were made to co-crystalize hNurr1-LBD$^{323-593}$ (Nurr1-LBD) in complex with PGA1 and PGA2. The crystal structure of the Nurr1-LBD in complex with PGA1 (FIG. 5a) and PGA2 (FIG. 5b) has been determined up to 2.0 Å and 2.34 Å, in orthorhombic space groups P21212 and P212121 with two and four molecules in the asymmetric unit, respectively. The important H12 helix, carrying the functional AF2 region, has been displaced by 23° and 19° away from the protein core in the PGA1 (FIG. 6a) and PGA2 (FIG. 6b) bound forms, with respect to its apo form, respectively. This reorientation, induced by PGs binding, creates a cavity packed by helices H4, H11 and H12, wherein the C20 end of PGA1/PGA2 docks itself forming hydrophobic contacts with Ser441 and Leu440 of H4, Ile573 and Leu570 of H11 and Leu591 and Thr595 of H12. The hydroxyl oxygen forms a hydrogen bond with the main chain nitrogen of Leu444. The oxygen attached to the cyclopentenone ring forms a hydrogen bond with the sidechain of Thr567. In addition, the most important feature is the covalent bond formed by the C11 carbon with the sidechain sulphur (SG) of Cys566 at ~1.7 Å due to Michael addition reaction, confirmed by the continuous electron density between these atoms. As mentioned above, the movement of H12 by 23°/19° is the key conformational change due to PG binding (FIG. 6). This shift is accompanied by an alteration in the electrostatic surface potential near this region, proposed to be responsible for co-regulator binding. Thus this structural switch might be responsible for Nurr1's transactivation mechanism. Apart from this region, we also observed an expansion of the surface pocket at the H10-H11 wedge region, quantified by increase of 10 Å$^2$ in its area in comparison with the apo form.

Example 5: Covalent Binding of PGs to Nurr1

Figure 7:
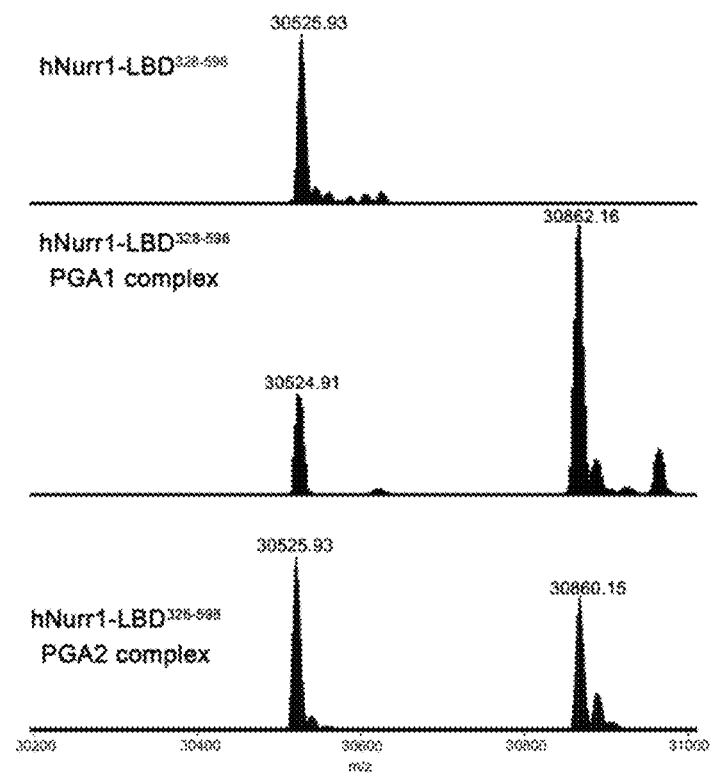
FIG. 7: Mass spectrometry data confirming that PGA1 and PGA2 are covalently attached to Nurr1. The MS data for hNurr1-LBD in apo (top), PGA1 (middle) and PGA2 (bottom) bound forms reveal the presence of the protein-ligand complex formed by covalent attachment. This is confirmed by the combined molecular mass of 30862 and 30860 Da for Nurr1 bound with PGA1 and PGA2 respectively. (The molecular weights of hNurr1-LBD, PGA1 and PGA2 are 30.5 kDa, 336.5 Da and 334.45 Da, respectively).

To exclude the possibility that the covalent coupling of PGA1/PGA2 to human Nurr1-LBD domain seen in the crystal structures was an artifact of crystallization or exposure to high-intensity X-rays, Nurr1-LBD at ~ 300 μM prepared in 0.1% FA in water was analyzed using a Dionex UltiMate 3000 UHPLC coupled to a linear quadrupole ion trap-Fourier transform Ultra apparatus (LTQ-FT Ultra, Thermo Scientific Inc.). Protein solution (5 μL) was injected directly into the detector carried by 0.1% FA in water. On-line ionization was performed using a Michrom CaptiveSpray ion source (Bruker-Michrom Inc., Auburn, USA)

at an electrospray potential of 1.5 kV and capillary temperature of 200° C. The inventors showed that the mass for Nurr1-LBD is 30525 Da, which is consistent with the calculated mass of Nurr1-LBD, 30.5 kDa. For analysis of ligand-bound Nurr1-LBD, Nurr1-LBD was incubated overnight with PGA1 and PGA2 at 1:1.5 molar ratio. The data showed the appearance of a protein-ligand complex with mass shift by 336.5 Da and 334.45 Da at 30862 and 30860 (FIG. 7), confirming that, under the condition used in the study about 50% of Nurr1 binds PGA1 or PGA2 covalently. These data suggest that crystal structures of Nurr1-LBD in complex with PGA1 or PGA2 are not a crystallization artifact. It supports the biological relevance of the observations of covalent coupling in the Nurr1-mediated transcriptional regulation by cyclopentenone prostaglandins.

Example 6: Design and Docking of PG Derivative to Nurr1

Figure 8:
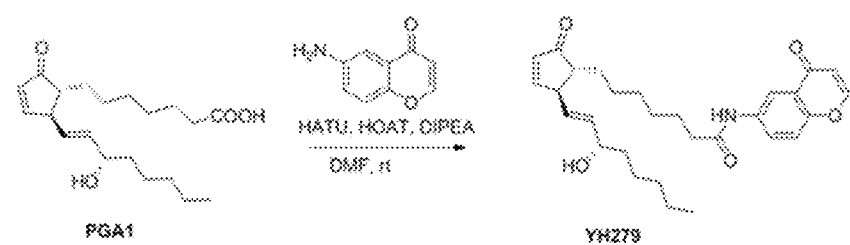
FIG. 8: Chemical synthesis of a prostaglandin derivative (YH279) and its docking pose with Nurr-LBD. (Top) The chemical synthesis scheme adopted to obtain YH279 by linking the carboxyl end of PGA1 with 6-amino-4H-chromen-4-one fragment, designed based on the observation of the secondary site in the PGA1/PGA2 bound Nurr1-LBD structures. (Bottom) The docking pose of YH279 into the Nurr1-LBD, with the linked fragment fitting well into the secondary site. The main interactions made by the fragment are shown in broken lines while the relative positions of all the residues in this secondary site are labelled, accordingly.
Figure 8:
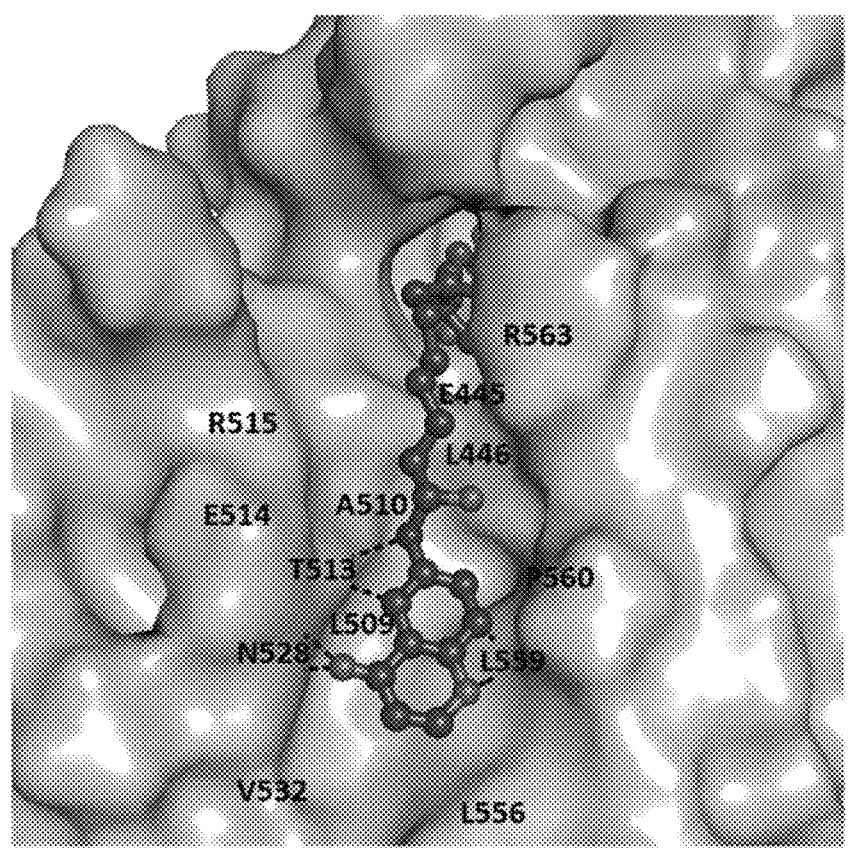

A surface pocket, near the carobyxl end of PGA1/PGA2, made up of residues Glu445, Leu446, Leu509, Ala510, Thr513, Glu514, Arg515, Gln528, Val532, Leu556, Leu559, Pro560 and Arg563 (H10-H11 wedge region) was identified from the PGA1/PGA2 bound Nurr1-LBD structures. The inventors coined this pocket as the 'secondary site' and used it for designing the prostaglandin derivative, wherein fragments which can bind to this site was screened to be chemically linked to the cyclopentanone prostaglandin, the lead molecule. To start with, the inventors identified a fragment, 6-amino-4H-chromen-4-one and linked it with PGA1's carboxyl end (YH279) by chemical synthesis (FIG. 8). Briefly, to a stirred solution of PGA1 (5 mg, 0.015 mmol), HATU (6.2 mg, 0.017 mmol) and HOAT (2.3 mg, 0.017 mmol) in 1 ml DMF, diisopropylethyl amine (7.8 µl, 0.045 mmol) was added and stirred at room temperature for 15 minutes. Then 6-amino-4H-chromen-4-one (4.8 mg, 0.030 mmol) was added to the solution and stirred for 2 hours. TLC was used to monitor the reaction. After consuming PGA1, the solvent was removed under reduced pressure and the crude was submitted to preparative TLC (Hexane:EtOAc=1:1). YH279 was obtained as colorless oil (4.5 mg) in a yield of 62%. $^1$H NMR (500 MHz, CDCl$_3$) δ 8.72 (brs, 1H), 8.51 (dd, J=9.2, 2.9 Hz, 1H), 8.06 (d, J=2.8 Hz, 1H), 7.89 (d, J=5.9 Hz, 1H), 7.54-7.42 (m, 2H), 6.30 (d, J=5.9 Hz, 1H), 6.15 (dd, J=5.7, 2.2 Hz, 1H), 5.67-5.57 (m, 2H), 4.09 (q, J=5.9, 4.9 Hz, 1H), 3.22 (dp, J=4.6, 2.4 Hz, 1H), 2.44 (t, J=7.5 Hz, 2H), 2.07 (qd, J=5.2, 3.3, 2.8 Hz, 1H), 1.99 (brs, 1H), 1.62-1.40 (m, 4H), 1.40-1.11 (m, 14H); $^{13}$C NMR (126 MHz, CDCl$_3$) δ 211.62, 177.85, 172.28, 165.24, 155.86, 153.00, 136.63, 135.12, 133.35, 130.45, 126.93, 124.98, 119.03, 114.78, 112.32, 72.46, 52.27, 50.74, 37.53, 37.45, 31.83, 30.41, 29.17, 29.00, 26.97, 25.45, 25.22, 22.72, 14.15; ESI-MS m/z [M+Na]$^+$=502.55. For the in silico docking of YH279 on Nurr1-LBD, the inventors built and regularized the ligand YH279 using the JLigand module (Lebedev, et al. Acta Crystallogr D Biol Crystallogr 68, 431-440 (2012)) under the CCP4 suite of programs (Winn, et al. Acta Crystallogr D Biol Crystallogr 67, 235-242 (2011)). Then, using the software PyMOL (DeLano Scientific, Palo Alto, CA, USA) YH279 was docked into Nurr1-LBD manually, guided by the Nurr1-LBD-PGA1 complex. Finally, the Nurr1-LBD-YH279 complex was subjected to 1000 cycles of energy minimization using the 'Minimize Structure' module in the software Chimera (Pettersen, et al. J Comput Chem. 25, 1605-1612, (2004)), to remove any short-contacts between the protein and ligand atoms, if any. The resulting model revealed that the linked fragment fits well into the secondary site (FIG. 8) making key interactions with the neighbouring residues.

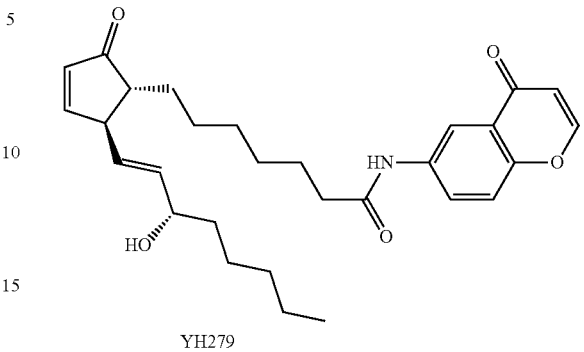

YH279

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A method of modulating a Nurr1, the method comprising contacting the Nurr1 with an effective amount of a cyclopentenone prostaglandin derivative, wherein the cyclopentenone prostaglandin derivative YH279:

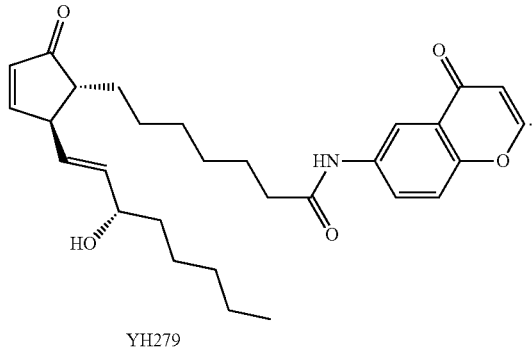 [SMILES: CCCCC[C@H](O)/C=C/[C@H]1C=CC(=O)[C@@H]1CCCCCCC(=O)Nc1ccc2occc(=O)c2c1 ; "YH279"]

YH279

2. The method of claim 1, wherein the method further comprises administering to a subject suffering from a disease, disorder or condition associated with a Nurr1, an effective amount of the cyclopentenone prostaglandin derivative, for treating a disease, disorder or condition associated with a Nurr1 in the subject, wherein the disease, disorder or condition associated with Nurr1 is selected from the group consisting of cancer, rheumatoid arthritis, Alzheimer's disease, schizophrenia, manic depression, Parkinson's disease, and combinations thereof.

3. The method of claim 2, wherein the subject is a mammal.

* * * * *

```
                              SEQUENCE LISTING

<160> NUMBER OF SEQ ID NOS: 5

<210> SEQ ID NO 1
<211> LENGTH: 271
<212> TYPE: PRT
<213> ORGANISM: Homo sapiens

<400> SEQUENCE: 1

Met Val Lys Glu Val Val Arg Thr Asp Ser Leu Lys Gly Arg Arg Gly
1               5                   10                  15

Arg Leu Pro Ser Lys Pro Lys Ser Pro Gln Glu Pro Ser Pro Pro Ser
            20                  25                  30

Pro Pro Val Ser Leu Ile Ser Ala Leu Val Arg Ala His Val Asp Ser
        35                  40                  45

Asn Pro Ala Met Thr Ser Leu Asp Tyr Ser Arg Phe Gln Ala Asn Pro
    50                  55                  60

Asp Tyr Gln Met Ser Gly Asp Asp Thr Gln His Ile Gln Gln Phe Tyr
65                  70                  75                  80

Asp Leu Leu Thr Gly Ser Met Glu Ile Ile Arg Gly Trp Ala Glu Lys
                85                  90                  95

Ile Pro Gly Phe Ala Asp Leu Pro Lys Ala Asp Gln Asp Leu Leu Phe
            100                 105                 110

Glu Ser Ala Phe Leu Glu Leu Phe Val Leu Arg Leu Ala Tyr Arg Ser
            115                 120                 125

Asn Pro Val Glu Gly Lys Leu Ile Phe Cys Asn Gly Val Val Leu His
        130                 135                 140

Arg Leu Gln Cys Val Arg Gly Phe Gly Glu Trp Ile Asp Ser Ile Val
145                 150                 155                 160

Glu Phe Ser Ser Asn Leu Gln Asn Met Asn Ile Asp Ile Ser Ala Phe
                165                 170                 175

Ser Cys Ile Ala Ala Leu Ala Met Val Thr Glu Arg His Gly Leu Lys
            180                 185                 190

Glu Pro Lys Arg Val Glu Glu Leu Gln Asn Lys Ile Val Asn Cys Leu
            195                 200                 205

Lys Asp His Val Thr Phe Asn Asn Gly Gly Leu Asn Arg Pro Asn Tyr
        210                 215                 220

Leu Ser Lys Leu Leu Gly Lys Leu Pro Glu Leu Arg Thr Leu Cys Thr
225                 230                 235                 240

Gln Gly Leu Gln Arg Ile Phe Tyr Leu Lys Leu Glu Asp Leu Val Pro
                245                 250                 255

Pro Pro Ala Ile Ile Asp Lys Leu Phe Leu Asp Thr Leu Pro Phe
            260                 265                 270

<210> SEQ ID NO 2
<211> LENGTH: 271
<212> TYPE: PRT
<213> ORGANISM: Mus musculus

<400> SEQUENCE: 2

Met Val Lys Glu Val Val Arg Thr Asp Ser Leu Lys Gly Arg Arg Gly
1               5                   10                  15

Arg Leu Pro Ser Lys Pro Lys Ser Pro Gln Asp Pro Ser Pro Pro Ser
            20                  25                  30

Pro Pro Val Ser Leu Ile Ser Ala Leu Val Arg Ala His Val Asp Ser
```

```
                35                  40                  45
Asn Pro Ala Met Thr Ser Leu Asp Tyr Ser Arg Phe Gln Ala Asn Pro
 50                  55                  60

Asp Tyr Gln Met Ser Gly Asp Thr Gln His Ile Gln Gln Phe Tyr
 65                  70                  75                  80

Asp Leu Leu Thr Gly Ser Met Glu Ile Ile Arg Gly Trp Ala Glu Lys
                 85                  90                  95

Ile Pro Gly Phe Ala Asp Leu Pro Lys Ala Asp Gln Asp Leu Leu Phe
                100                 105                 110

Glu Ser Ala Phe Leu Glu Leu Phe Val Leu Arg Leu Ala Tyr Arg Ser
                115                 120                 125

Asn Pro Val Glu Gly Lys Leu Ile Phe Cys Asn Gly Val Val Leu His
130                 135                 140

Arg Leu Gln Cys Val Arg Gly Phe Gly Glu Trp Ile Asp Ser Ile Val
145                 150                 155                 160

Glu Phe Ser Ser Asn Leu Gln Asn Met Asn Ile Asp Ile Ser Ala Phe
                165                 170                 175

Ser Cys Ile Ala Ala Leu Ala Met Val Thr Glu Arg His Gly Leu Lys
                180                 185                 190

Glu Pro Lys Arg Val Glu Glu Leu Gln Asn Lys Ile Val Asn Cys Leu
                195                 200                 205

Lys Asp His Val Thr Phe Asn Asn Gly Gly Leu Asn Arg Pro Asn Tyr
210                 215                 220

Leu Ser Lys Leu Leu Gly Lys Leu Pro Glu Leu Arg Thr Leu Cys Thr
225                 230                 235                 240

Gln Gly Leu Gln Arg Ile Phe Tyr Leu Lys Leu Glu Asp Leu Val Pro
                245                 250                 255

Pro Pro Ala Ile Ile Asp Lys Leu Phe Leu Asp Thr Leu Pro Phe
                260                 265                 270

<210> SEQ ID NO 3
<211> LENGTH: 598
<212> TYPE: PRT
<213> ORGANISM: Homo sapiens

<400> SEQUENCE: 3

Met Pro Cys Val Gln Ala Gln Tyr Gly Ser Ser Pro Gln Gly Ala Ser
 1                5                  10                  15

Pro Ala Ser Gln Ser Tyr Ser Tyr His Ser Ser Gly Glu Tyr Ser Ser
                 20                  25                  30

Asp Phe Leu Thr Pro Glu Phe Val Lys Phe Ser Met Asp Leu Thr Asn
                 35                  40                  45

Thr Glu Ile Thr Ala Thr Thr Ser Leu Pro Ser Phe Ser Thr Phe Met
 50                  55                  60

Asp Asn Tyr Ser Thr Gly Tyr Asp Val Lys Pro Pro Cys Leu Tyr Gln
 65                  70                  75                  80

Met Pro Leu Ser Gly Gln Gln Ser Ser Ile Lys Val Glu Asp Ile Gln
                 85                  90                  95

Met His Asn Tyr Gln Gln His Ser His Leu Pro Pro Gln Ser Glu Glu
                100                 105                 110

Met Met Pro His Ser Gly Ser Val Tyr Tyr Lys Pro Ser Ser Pro Pro
                115                 120                 125

Thr Pro Thr Thr Pro Gly Phe Gln Val Gln His Ser Pro Met Trp Asp
                130                 135                 140
```

```
Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
            340                 345                 350

Gln Glu Pro Ser Pro Pro Ser Pro Val Ser Leu Ile Ser Ala Leu
        355                 360                 365

Val Arg Ala His Val Asp Ser Asn Pro Ala Met Thr Ser Leu Asp Tyr
    370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
    530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
```

```
                    565                 570                 575
Lys Leu Glu Asp Leu Val Pro Pro Ala Ile Ile Asp Lys Leu Phe
                580                 585                 590

Leu Asp Thr Leu Pro Phe
            595

<210> SEQ ID NO 4
<211> LENGTH: 598
<212> TYPE: PRT
<213> ORGANISM: Mus musculus

<400> SEQUENCE: 4

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Ser Thr Pro Ser Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335
```

-continued

Ser Leu Lys Gly Arg Arg Gly Arg Leu Pro Ser Lys Pro Lys Ser Pro
                340                 345                 350

Gln Asp Pro Ser Pro Pro Ser Pro Val Ser Leu Ile Ser Ala Leu
            355                 360                 365

Val Arg Ala His Val Asp Ser Asn Pro Ala Met Thr Ser Leu Asp Tyr
        370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
            435                 440                 445

Leu Arg Leu Ala Tyr Arg Ser Asn Pro Val Glu Gly Lys Leu Ile Phe
        450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
            515                 520                 525

Asn Lys Ile Val Asn Cys Leu Lys Asp His Val Thr Phe Asn Asn Gly
530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
            565                 570                 575

Lys Leu Glu Asp Leu Val Pro Pro Ala Ile Ile Asp Lys Leu Phe
            580                 585                 590

Leu Asp Thr Leu Pro Phe
        595

<210> SEQ ID NO 5
<211> LENGTH: 598
<212> TYPE: PRT
<213> ORGANISM: Rattus norvegicus

<400> SEQUENCE: 5

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

```
Met Met Pro His Ser Gly Ser Val Tyr Tyr Lys Pro Ser Pro Pro
            115                 120                 125

Thr Pro Ser Thr Pro Gly Phe Gln Val Gln His Ser Pro Met Trp Asp
130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
            195                 200                 205

Ser His His Val Val Asp Gly Gln Thr Phe Ala Val Pro Asn Pro Ile
        210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
        290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
                340                 345                 350

Gln Asp Pro Ser Pro Ser Pro Pro Val Ser Leu Ile Ser Ala Leu
            355                 360                 365

Val Arg Ala His Val Asp Ser Asn Pro Ala Met Thr Ser Leu Asp Tyr
        370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
            435                 440                 445

Leu Arg Leu Ala Tyr Arg Ser Asn Pro Val Glu Gly Lys Leu Ile Phe
450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
            485                 490                 495

Asn Ile Asp Ile Ser Ala Phe Ser Cys Ile Ala Ala Leu Ala Met Val
                500                 505                 510

Thr Glu Arg His Gly Leu Lys Glu Pro Lys Arg Val Glu Glu Leu Gln
            515                 520                 525
```

```
Asn Lys Ile Val Asn Cys Leu Lys Asp His Val Thr Phe Asn Asn Gly
    530             535                 540
Gly Leu Asn Arg Pro Asn Tyr Leu Ser Lys Leu Leu Gly Lys Leu Pro
545             550                 555                 560
Glu Leu Arg Thr Leu Cys Thr Gln Gly Leu Gln Arg Ile Phe Tyr Leu
                565                 570                 575
Lys Leu Glu Asp Leu Val Pro Pro Pro Ala Ile Ile Asp Lys Leu Phe
            580             585                 590
Leu Asp Thr Leu Pro Phe
            595
```